United States Patent
Schraga

(10) Patent No.: US 10,155,091 B2
(45) Date of Patent: Dec. 18, 2018

(54) PEN NEEDLE TIP AND METHOD OF MAKING AND USING THE SAME

(71) Applicant: STAT MEDICAL DEVICES, INC., N. Miami Beach, FL (US)

(72) Inventor: Steven Schraga, Surfside, FL (US)

(73) Assignee: STAT MEDICAL DEVICES, INC., North Miami Beach, FL (US)

( * ) Notice: Subject to any disclaimer, the term of this patent is extended or adjusted under 35 U.S.C. 154(b) by 8 days.

(21) Appl. No.: 14/795,330

(22) Filed: Jul. 9, 2015

(65) Prior Publication Data

US 2016/0008555 A1   Jan. 14, 2016

Related U.S. Application Data

(60) Provisional application No. 62/023,456, filed on Jul. 11, 2014.

(51) Int. Cl.
*A61M 5/50* (2006.01)
*A61M 5/34* (2006.01)
*A61M 5/32* (2006.01)

(52) U.S. Cl.
CPC ............ *A61M 5/344* (2013.01); *A61M 5/34* (2013.01); *A61M 5/3202* (2013.01); *A61M 5/3243* (2013.01); *A61M 5/50* (2013.01); *A61M 2005/3253* (2013.01); *A61M 2005/3254* (2013.01)

(58) Field of Classification Search
CPC ........ A61M 5/3243; A61M 2005/3253; A61M 2005/3254; A61M 5/002
See application file for complete search history.

(56) References Cited

U.S. PATENT DOCUMENTS 3,460,742 A * 8/1969 Langdon ............... A61M 5/002
                                                                206/439
4,894,055 A    1/1990 Sudnak
(Continued)

FOREIGN PATENT DOCUMENTS

EP    2 090 326         8/2009
FR    2684303 A1 *  6/1993 .......... A61M 5/3213
(Continued)

OTHER PUBLICATIONS

Translated description of FR 2684303.*

*Primary Examiner* — Nathan R Price
*Assistant Examiner* — Courtney Fredrickson
(74) *Attorney, Agent, or Firm* — Thomas | Horstemeyer, LLP

(57) ABSTRACT

A needle tip assembly for a pre-loaded syringe or a pen needle injection device, wherein the needle tip assembly comprises a needle mounted to a needle support. A body is sized and configured to receive therein the needle support and the needle. The body comprises a front portion, a rear portion, and an overall axial length that is greater than an axial length of the needle. Prior to the needle tip assembly being in an installed condition on the pre-loaded syringe or the pen needle injection device, each of the front portion covers a first puncturing end of the needle and the rear portion covers a second puncturing end of the needle. Prior to removal from the pre-loaded syringe or the pen needle injection device, the body is at least axially movably relative to the needle support to a position the front portion covers the first puncturing end.

20 Claims, 36 Drawing Sheets

(56) References Cited

U.S. PATENT DOCUMENTS

| | | | |
|---|---|---|---|
| 4,909,792 A | 3/1990 | Norelli | |
| 4,973,318 A | 11/1990 | Holm et al. | |
| 5,242,401 A | 9/1993 | Colsky | |
| 5,242,416 A | 9/1993 | Hutson | |
| 5,389,085 A | 2/1995 | D'Alessio et al. | |
| 5,419,773 A | 5/1995 | Rupp | |
| 5,454,828 A | 10/1995 | Schraga | |
| 5,591,138 A | 1/1997 | Vaillancourt | |
| 5,593,387 A | 1/1997 | Rupp | |
| 5,611,786 A | 3/1997 | Kirchhofer et al. | |
| 5,980,488 A | 11/1999 | Thorne | |
| 6,117,108 A | 9/2000 | Woehr et al. | |
| D445,602 S | 7/2001 | Tonon | |
| 6,287,278 B1 | 9/2001 | Woehr et al. | |
| 6,379,333 B1 | 4/2002 | Brimhall et al. | |
| 6,391,003 B1 | 5/2002 | Lesch, Jr. | |
| 6,460,234 B1 | 10/2002 | Gianchandani | |
| 6,470,754 B1 | 10/2002 | Gianchandani | |
| 6,616,630 B1 | 9/2003 | Woehr et al. | |
| 6,652,490 B2 | 11/2003 | Howell | |
| 6,749,588 B1 | 6/2004 | Howell et al. | |
| 6,855,129 B2 | 2/2005 | Jensen et al. | |
| 7,125,397 B2 | 10/2006 | Woehr et al. | |
| 7,160,269 B2 | 1/2007 | Woehr | |
| 7,214,211 B2 | 5/2007 | Woehr et al. | |
| 7,264,613 B2 | 9/2007 | Woehr et al. | |
| 7,462,168 B2 | 12/2008 | Stonehouse et al. | |
| 7,540,858 B2 | 6/2009 | DiBiasi | |
| 7,553,293 B2 | 6/2009 | Jensen et al. | |
| 7,871,397 B2 | 1/2011 | Schraga | |
| 8,597,255 B2 * | 12/2013 | Emmott | A61M 5/002 604/110 |
| 2002/0004648 A1 | 1/2002 | Larsen et al. | |
| 2002/0133122 A1 | 9/2002 | Giambattista et al. | |
| 2003/0014018 A1 | 1/2003 | Giambattista et al. | |
| 2003/0105431 A1 | 6/2003 | Howell | |
| 2003/0109832 A1 * | 6/2003 | Rindlisbacher | A61M 5/3216 604/192 |
| 2003/0195471 A1 | 10/2003 | Woehr et al. | |
| 2004/0116856 A1 | 6/2004 | Woehr et al. | |
| 2004/0186434 A1 | 9/2004 | Harding et al. | |
| 2004/0204681 A1 | 10/2004 | Thoresen et al. | |
| 2004/0220532 A1 | 11/2004 | Caizza | |
| 2004/0236284 A1 | 11/2004 | Hoste et al. | |
| 2004/0236288 A1 | 11/2004 | Howell | |
| 2005/0004532 A1 | 1/2005 | Woehr et al. | |
| 2005/0038392 A1 | 2/2005 | DeSalvo | |
| 2005/0080378 A1 | 4/2005 | Cindrich et al. | |
| 2005/0107748 A1 | 5/2005 | Thorne et al. | |
| 2005/0171485 A1 | 8/2005 | Larsen et al. | |
| 2005/0277881 A1 | 12/2005 | Sibbitt | |
| 2005/0277895 A1 | 12/2005 | Giambattista et al. | |
| 2005/0283115 A1 | 12/2005 | Giambattista et al. | |
| 2006/0229652 A1 | 10/2006 | Iio et al. | |
| 2006/0264828 A1 | 11/2006 | Woehr et al. | |
| 2007/0049868 A1 | 3/2007 | Woehr et al. | |
| 2007/0083159 A1 | 4/2007 | Woehr et al. | |
| 2007/0100297 A1 | 5/2007 | Woehr et al. | |
| 2007/0129689 A1 | 6/2007 | Woehr et al. | |
| 2007/0203458 A1 | 8/2007 | Tsubota | |
| 2007/0255225 A1 | 11/2007 | Alchas | |
| 2008/0108951 A1 | 5/2008 | Jerde et al. | |
| 2008/0154192 A1 * | 6/2008 | Schraga | A61M 5/347 604/110 |
| 2008/0177237 A1 | 7/2008 | Stonehouse et al. | |
| 2008/0177238 A1 | 7/2008 | Follman et al. | |
| 2009/0069753 A1 | 3/2009 | Ruan et al. | |
| 2009/0254042 A1 | 10/2009 | Gratwohl et al. | |
| 2010/0114035 A1 | 5/2010 | Schubert | |
| 2010/0292654 A1 | 11/2010 | Schraga | |
| 2011/0022001 A1 | 1/2011 | Wei | |
| 2011/0028909 A1 * | 2/2011 | Lum | A61M 5/34 604/192 |
| 2011/0077615 A1 | 3/2011 | Schraga | |
| 2011/0106016 A1 | 5/2011 | Wei | |
| 2011/0118667 A1 | 5/2011 | Zaiken et al. | |
| 2011/0160675 A1 | 6/2011 | Ruan et al. | |
| 2011/0288526 A1 | 11/2011 | Wei | |
| 2012/0226233 A1 * | 9/2012 | Schraga | A61M 5/3205 604/111 |

FOREIGN PATENT DOCUMENTS

| | | | |
|---|---|---|---|
| WO | WO 9521646 A1 * | 8/1995 | A61M 5/3271 |
| WO | 99/08742 | 2/1999 | |
| WO | 00/69501 | 11/2000 | |
| WO | 2008/077706 | 7/2008 | |

* cited by examiner

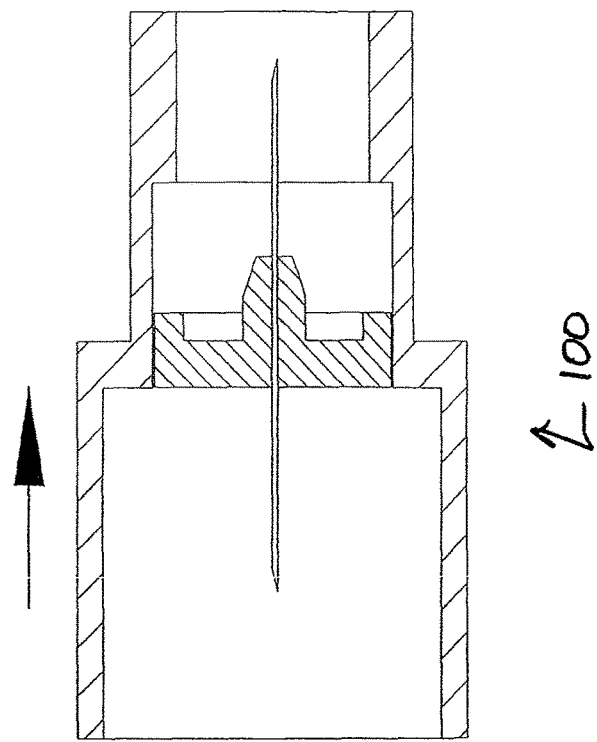
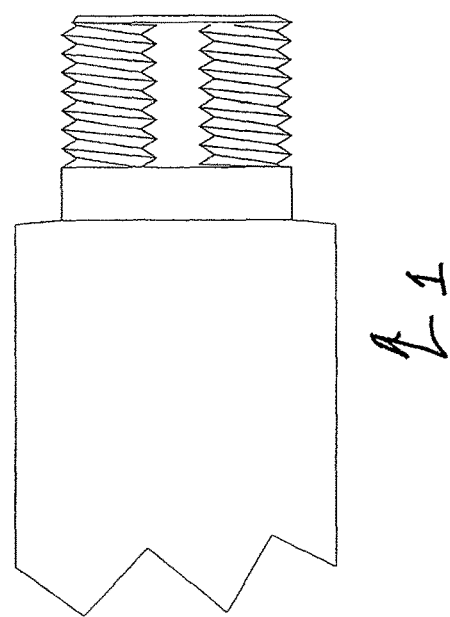
Fig. 6

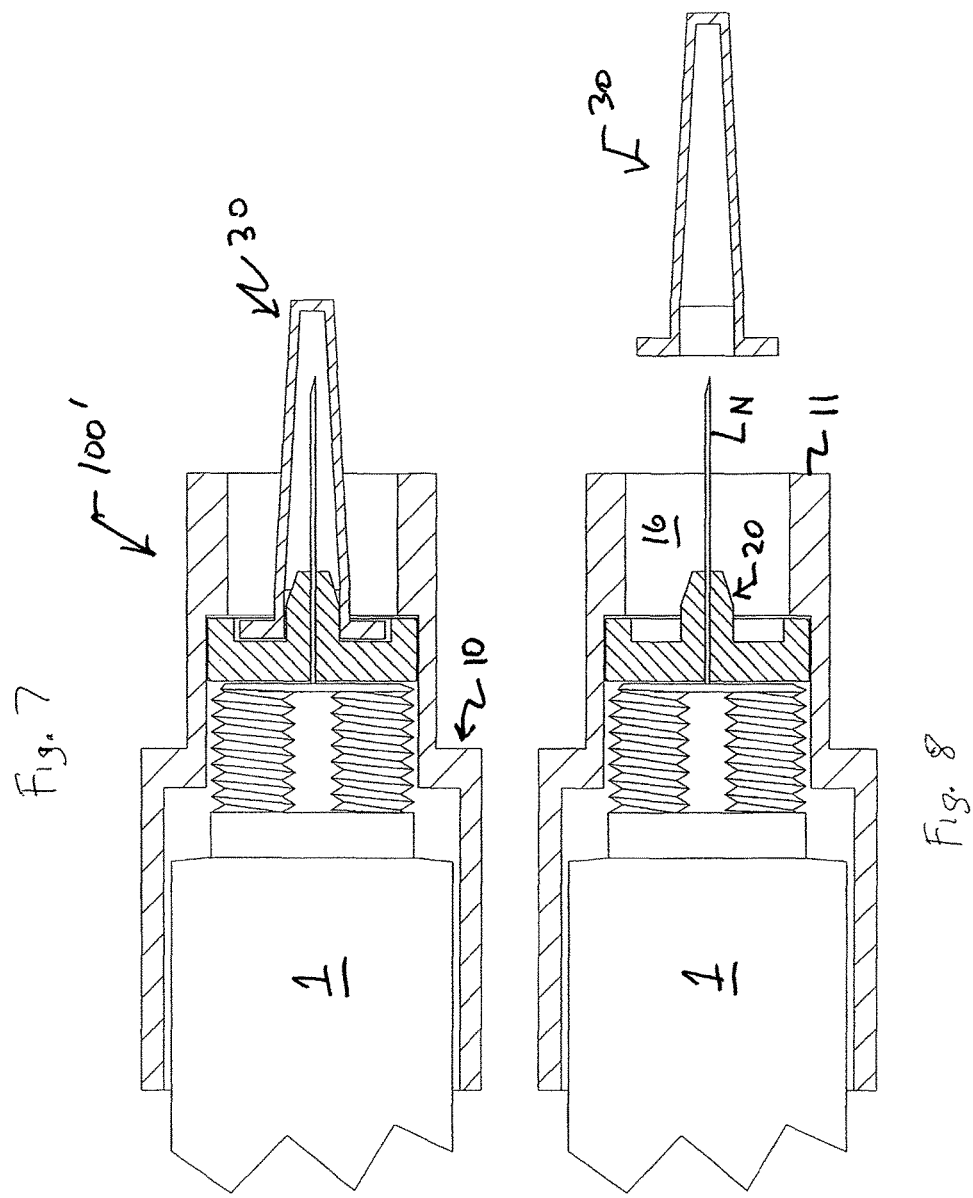

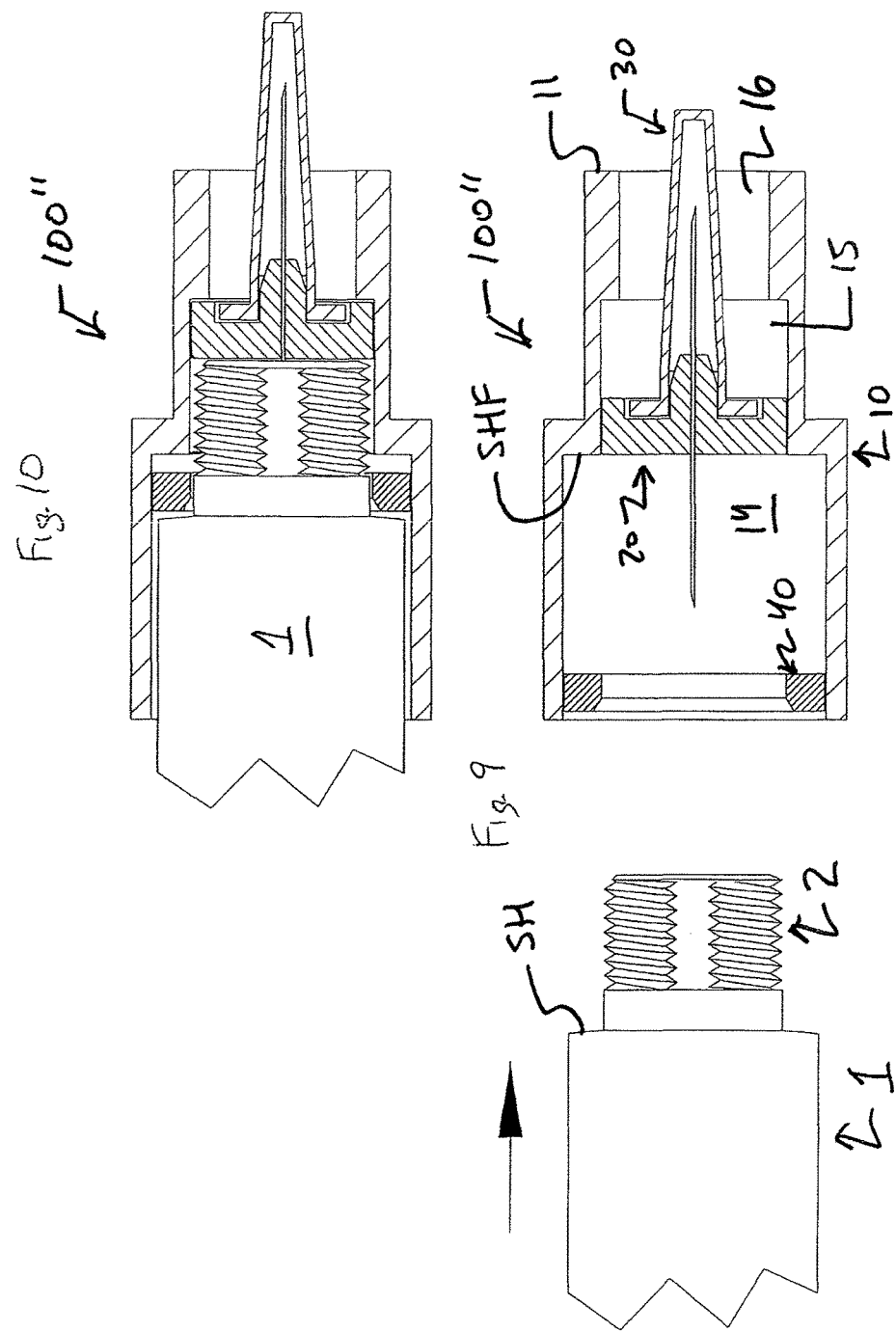

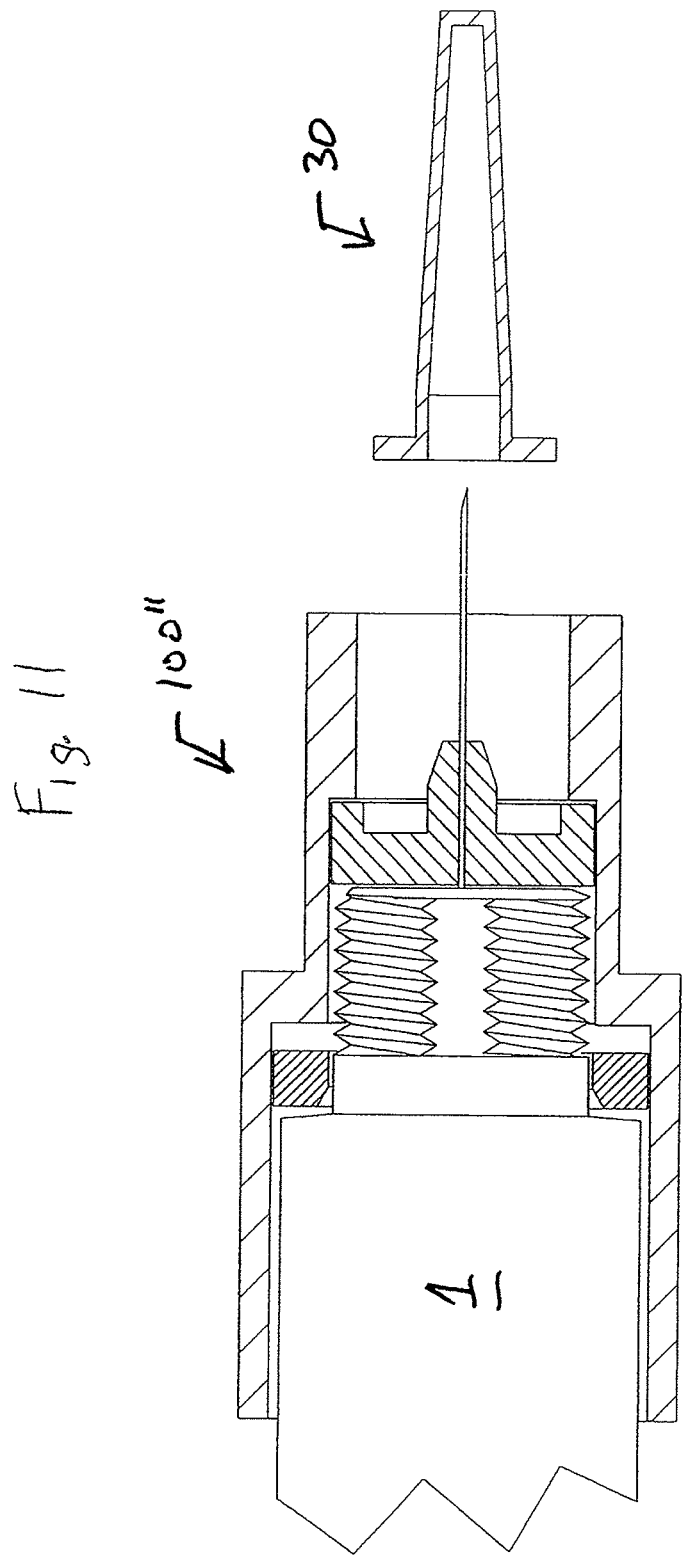

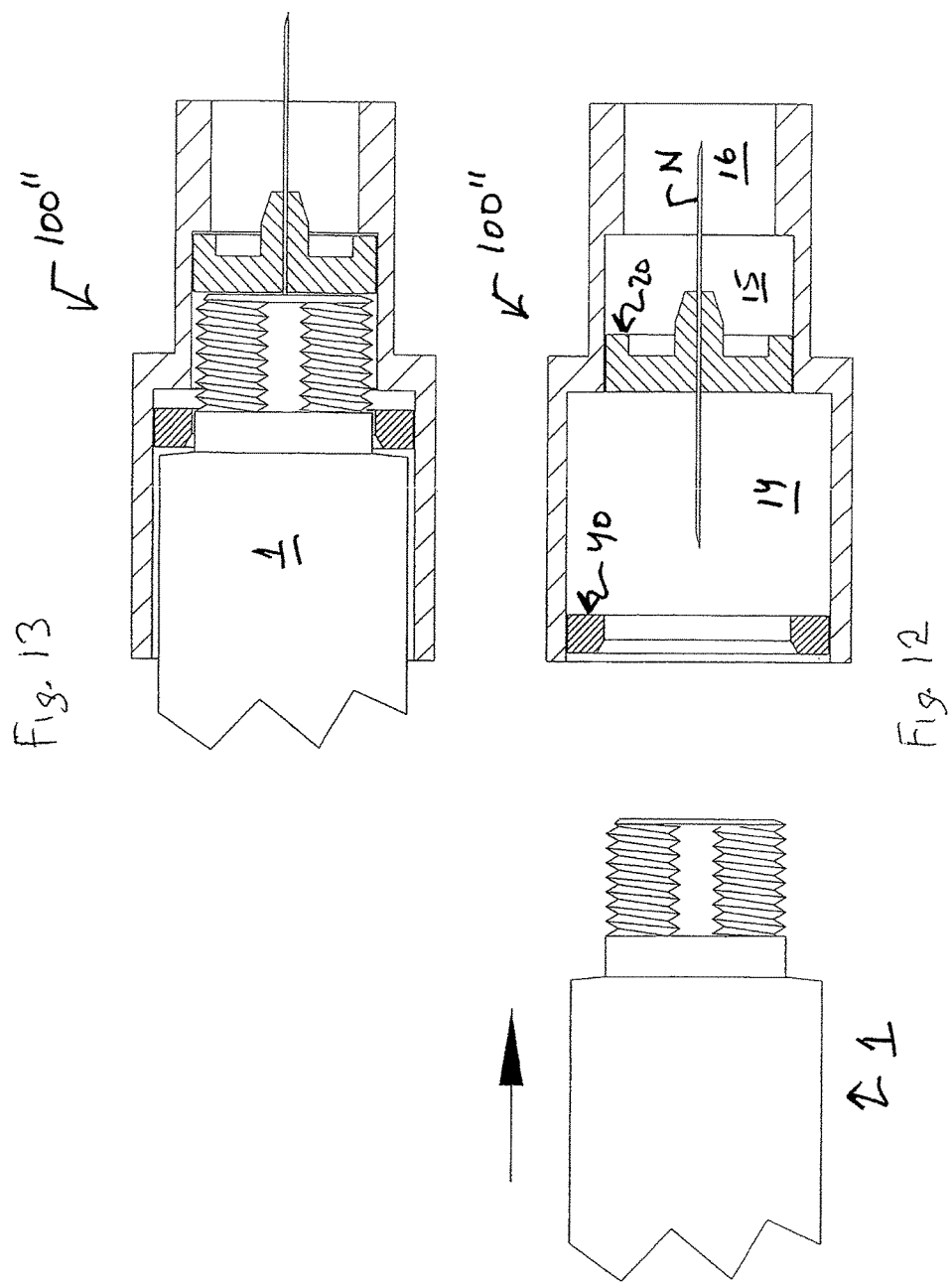

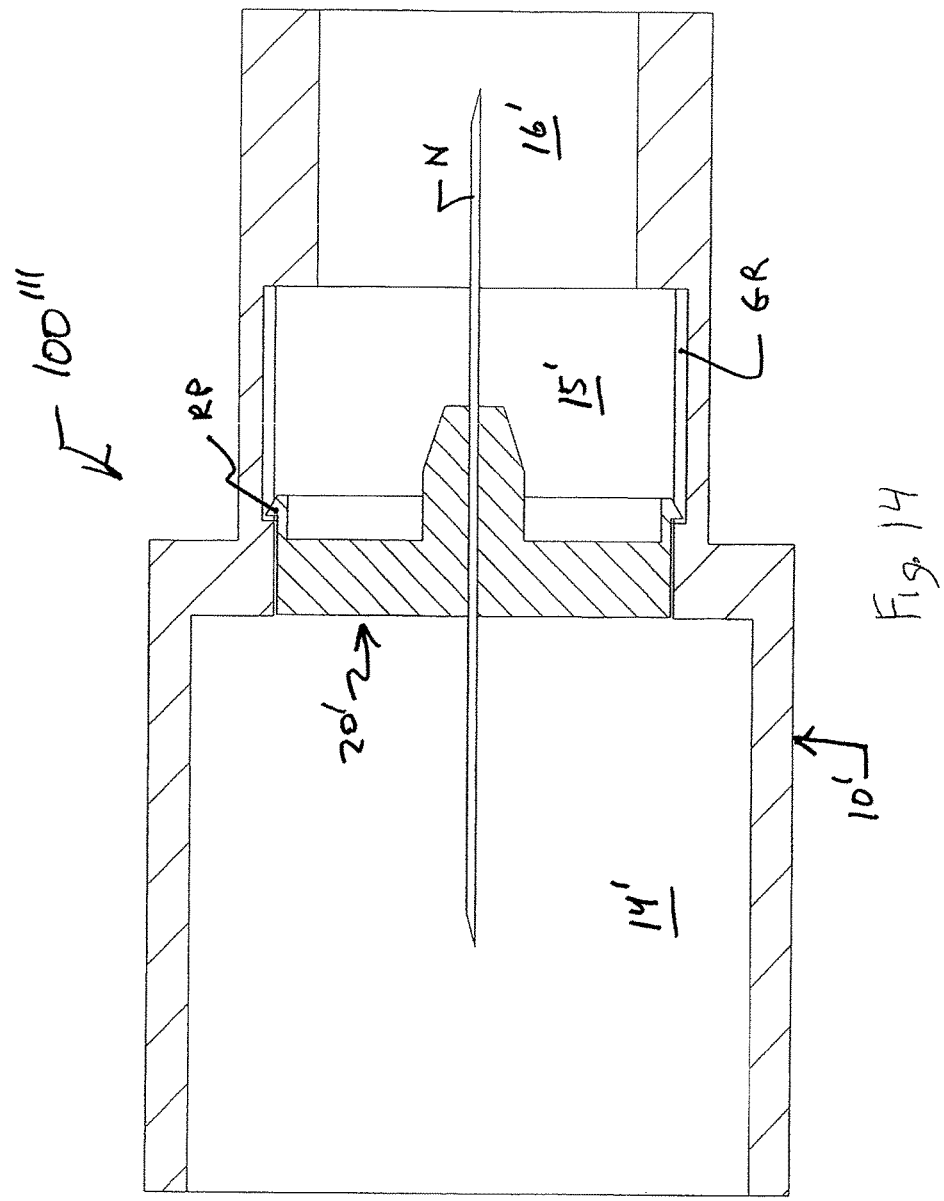

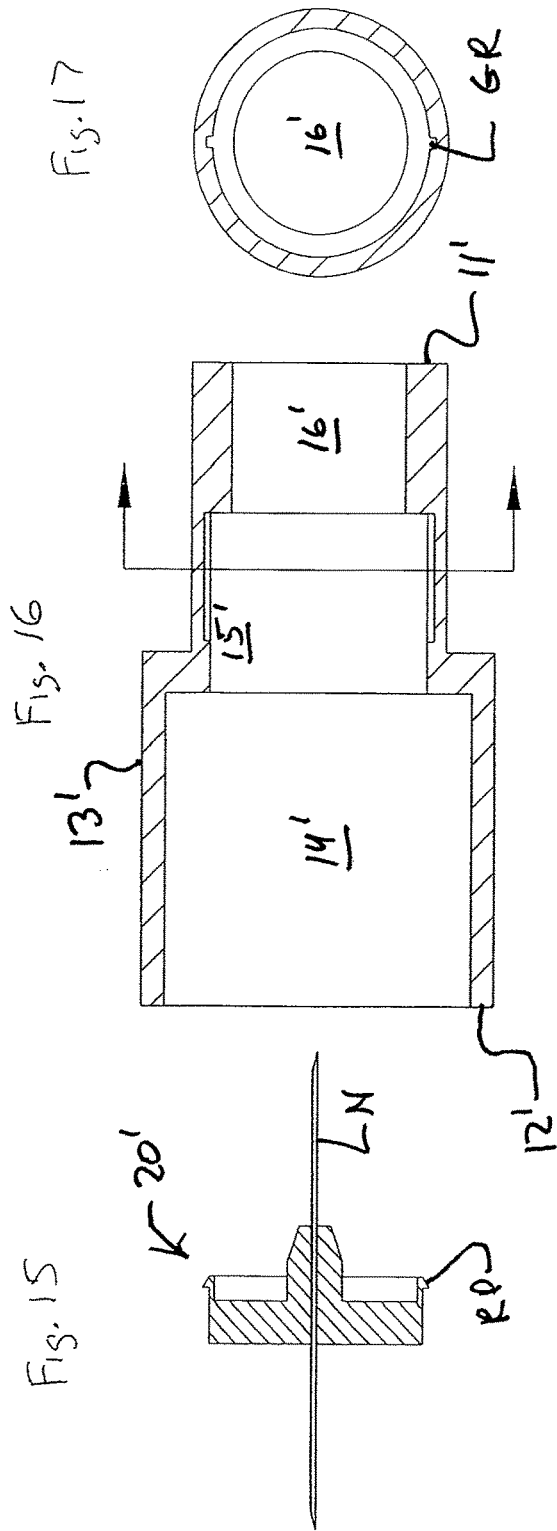

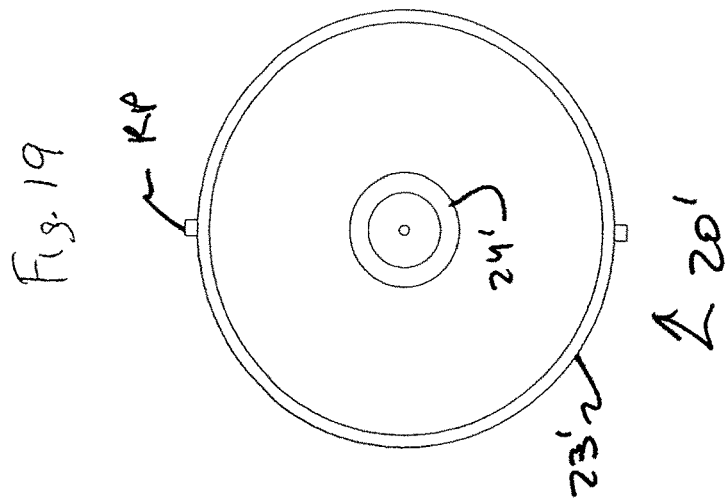
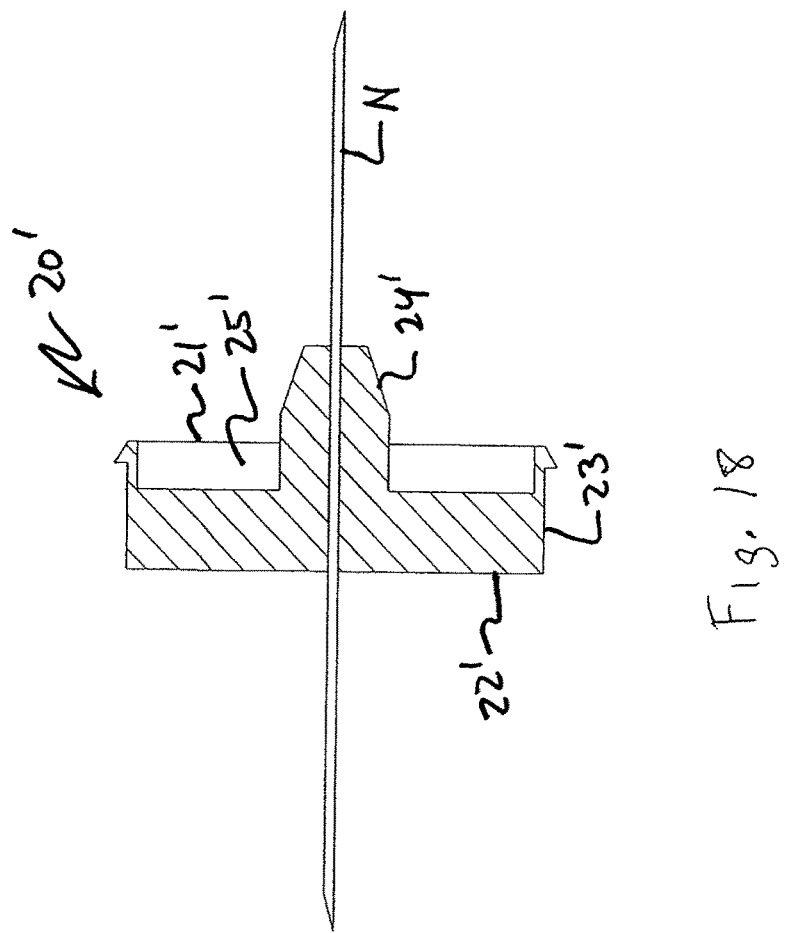

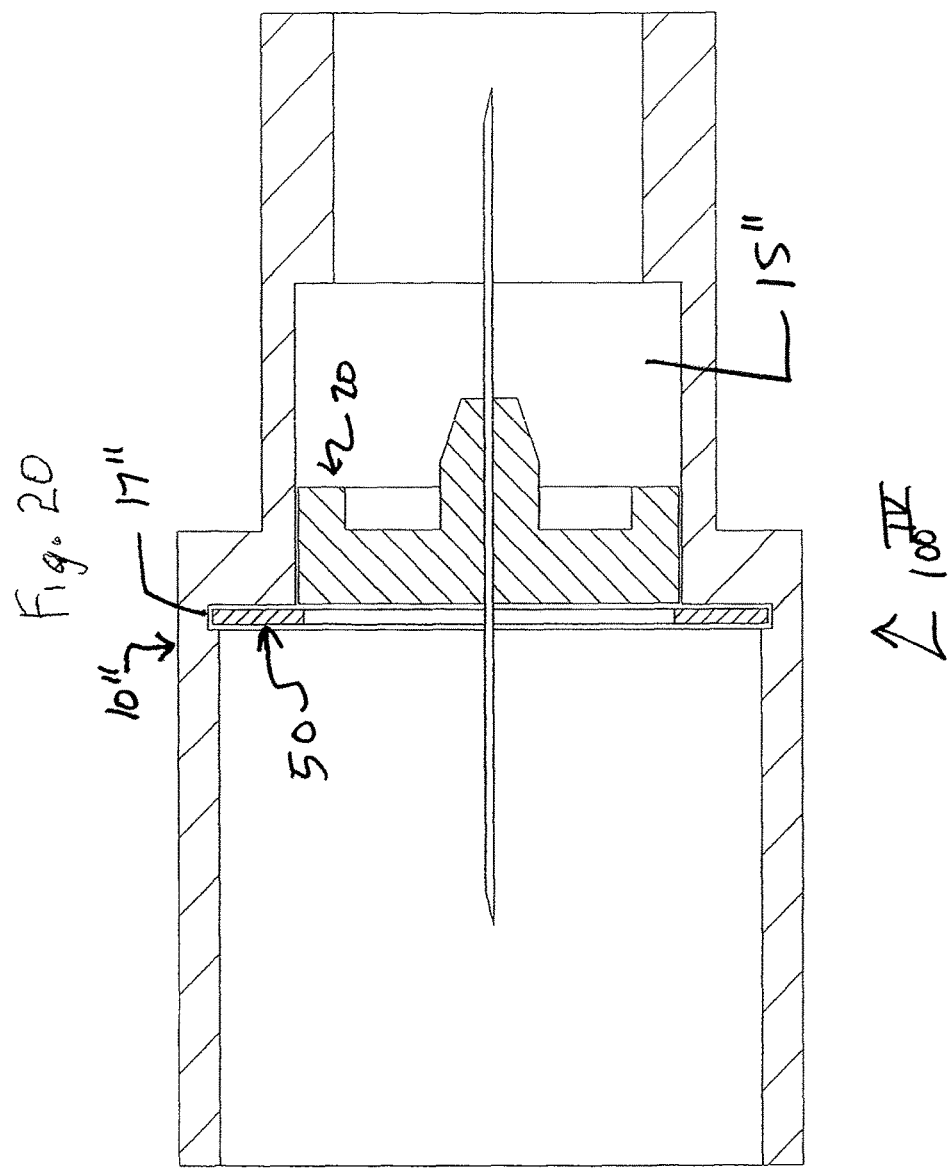

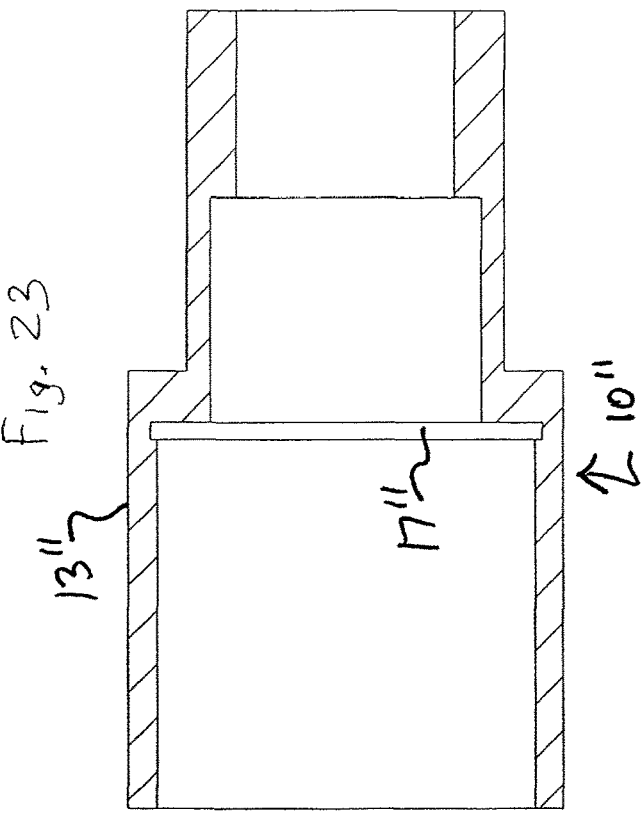
Fig. 23
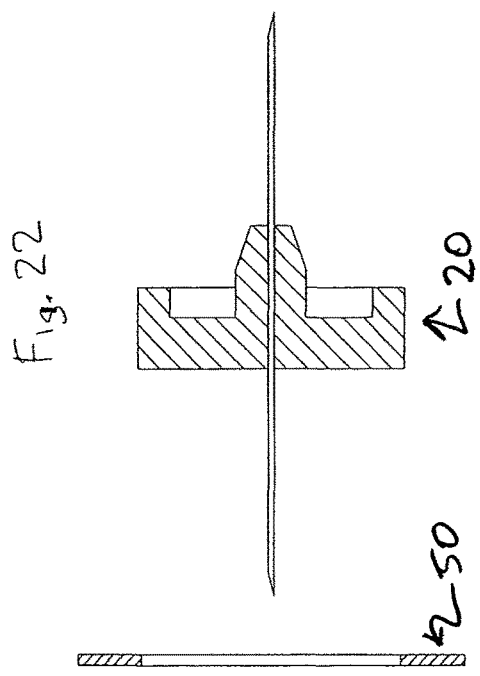
Fig. 22
Fig. 21

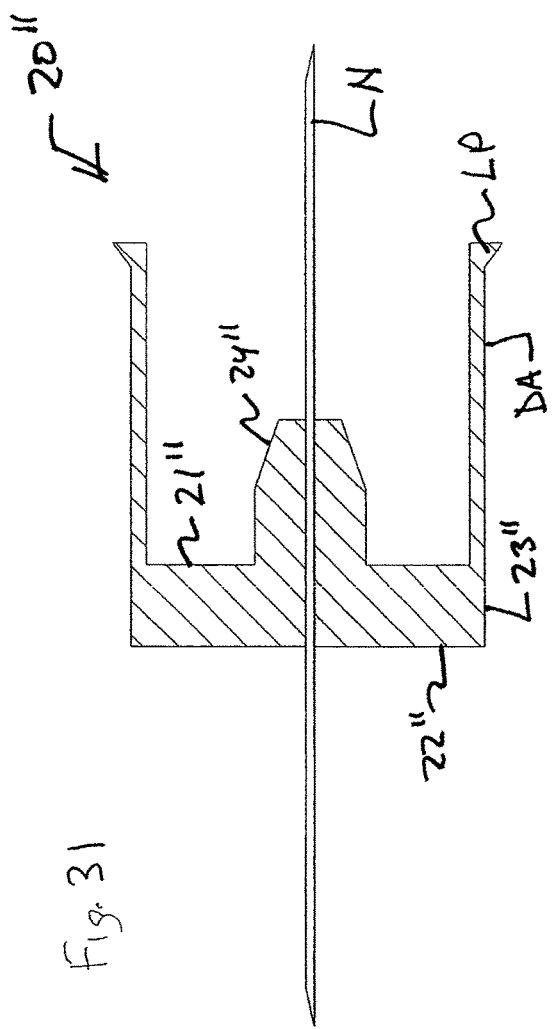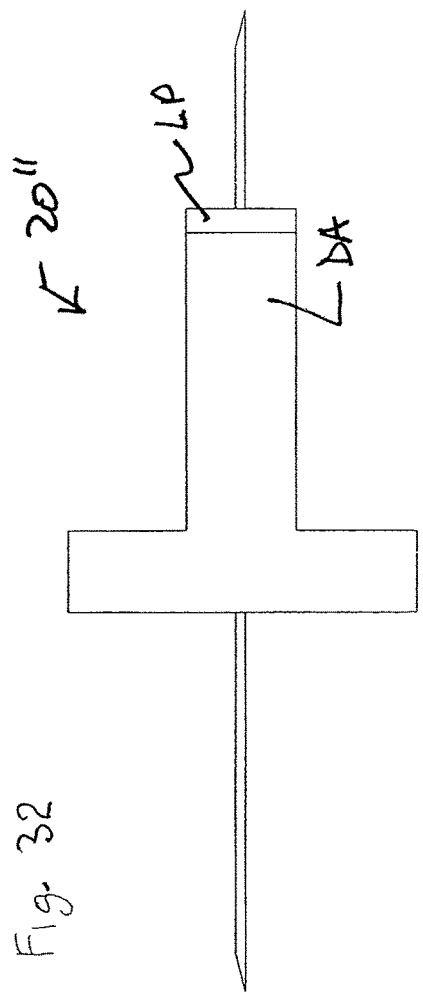
Fig. 31
Fig. 32

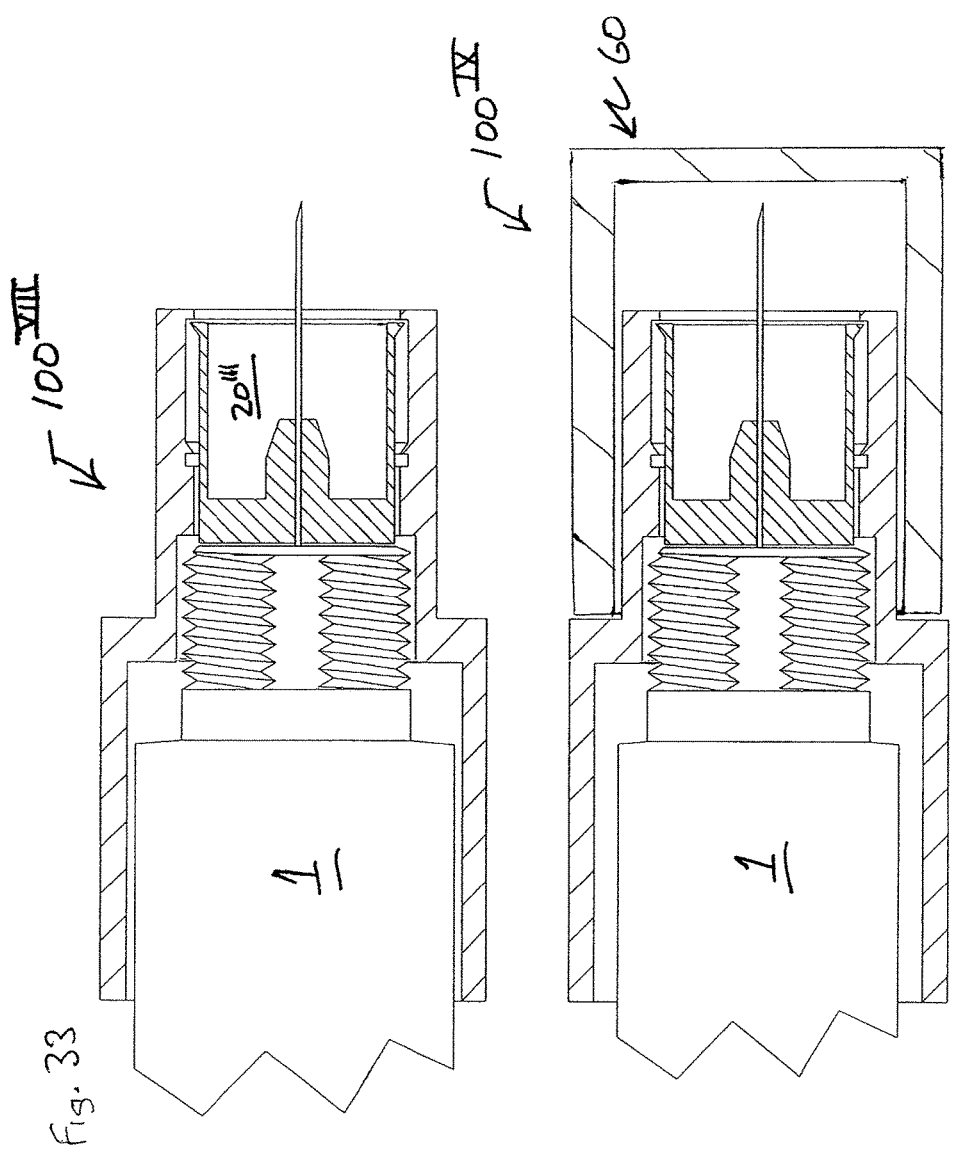

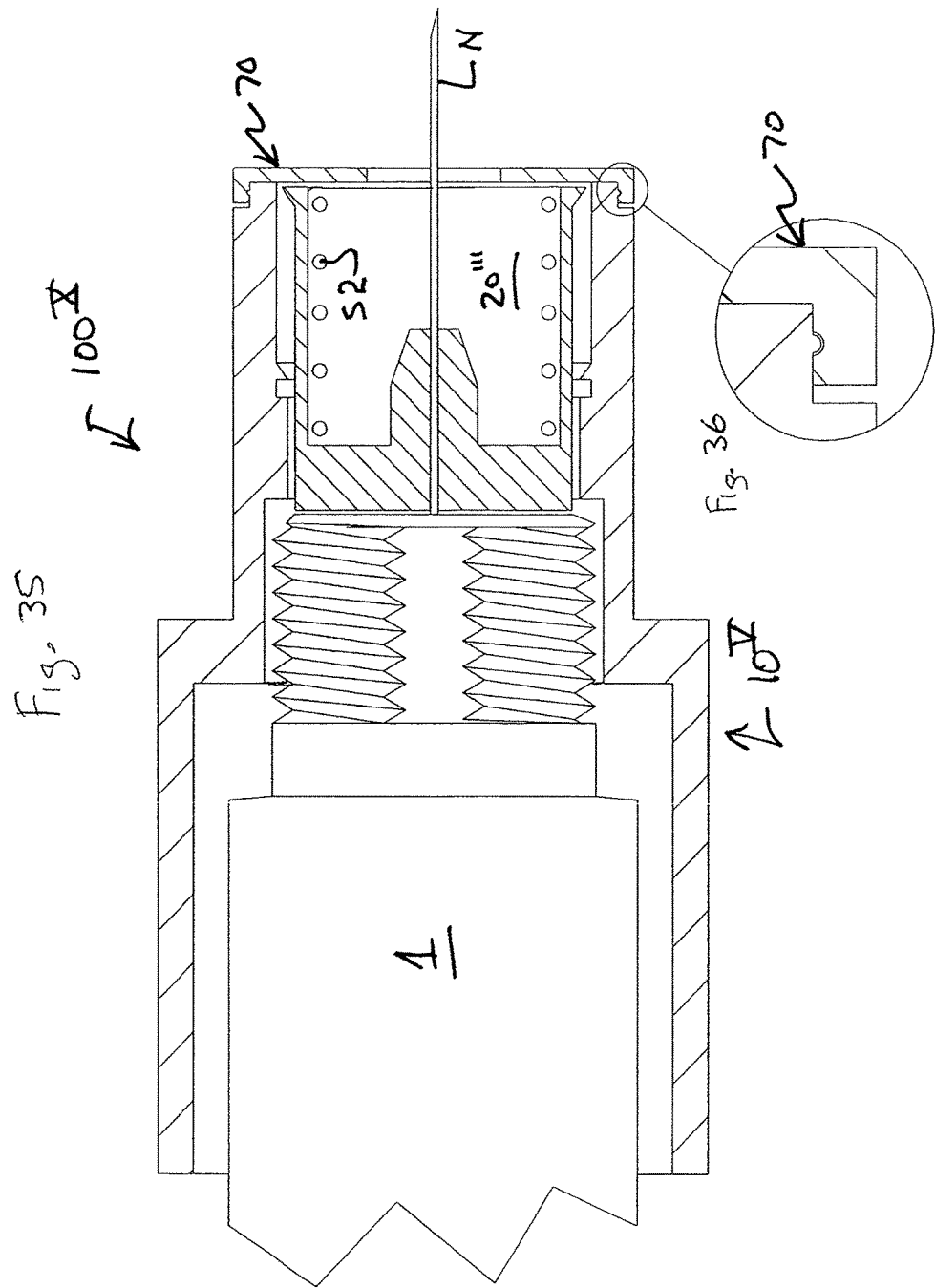

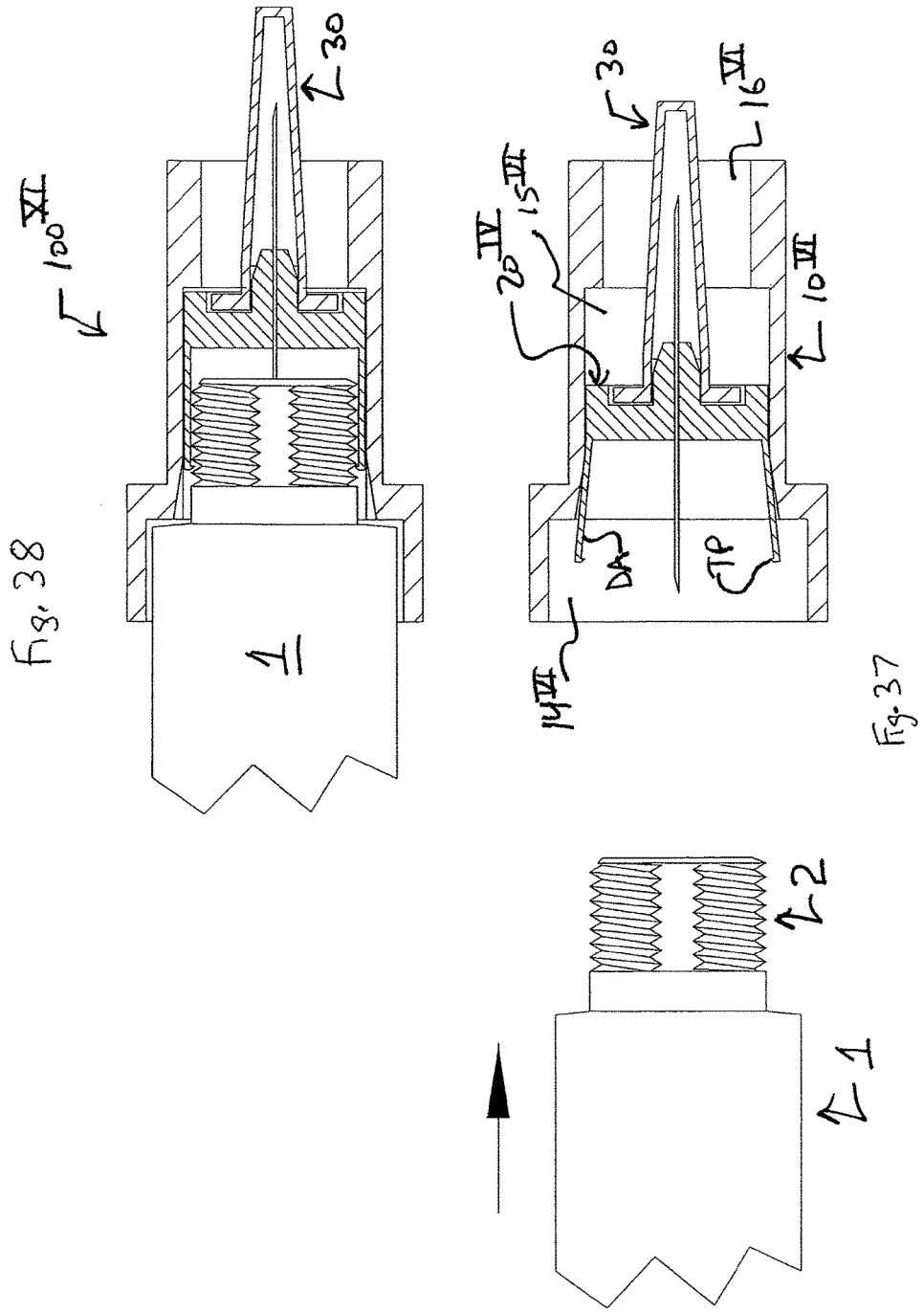

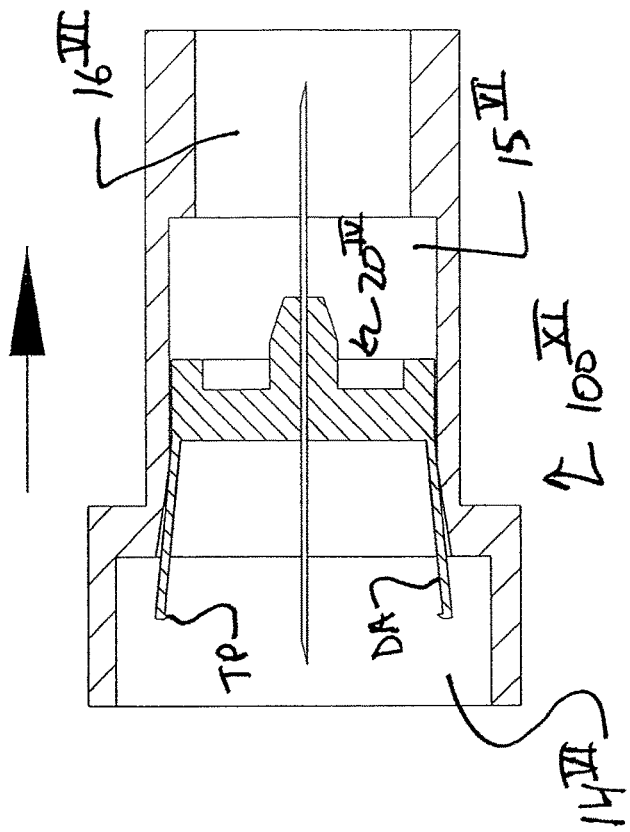
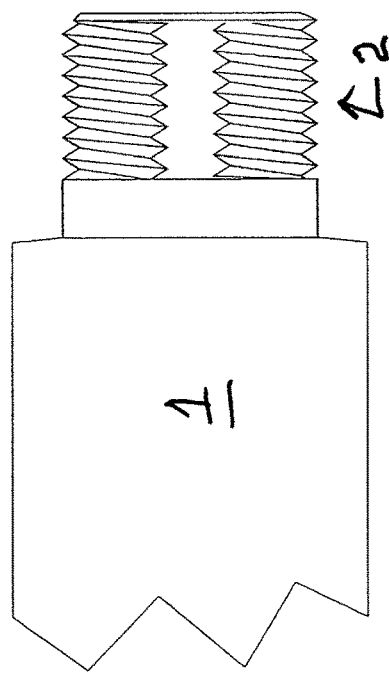
Fig. 39

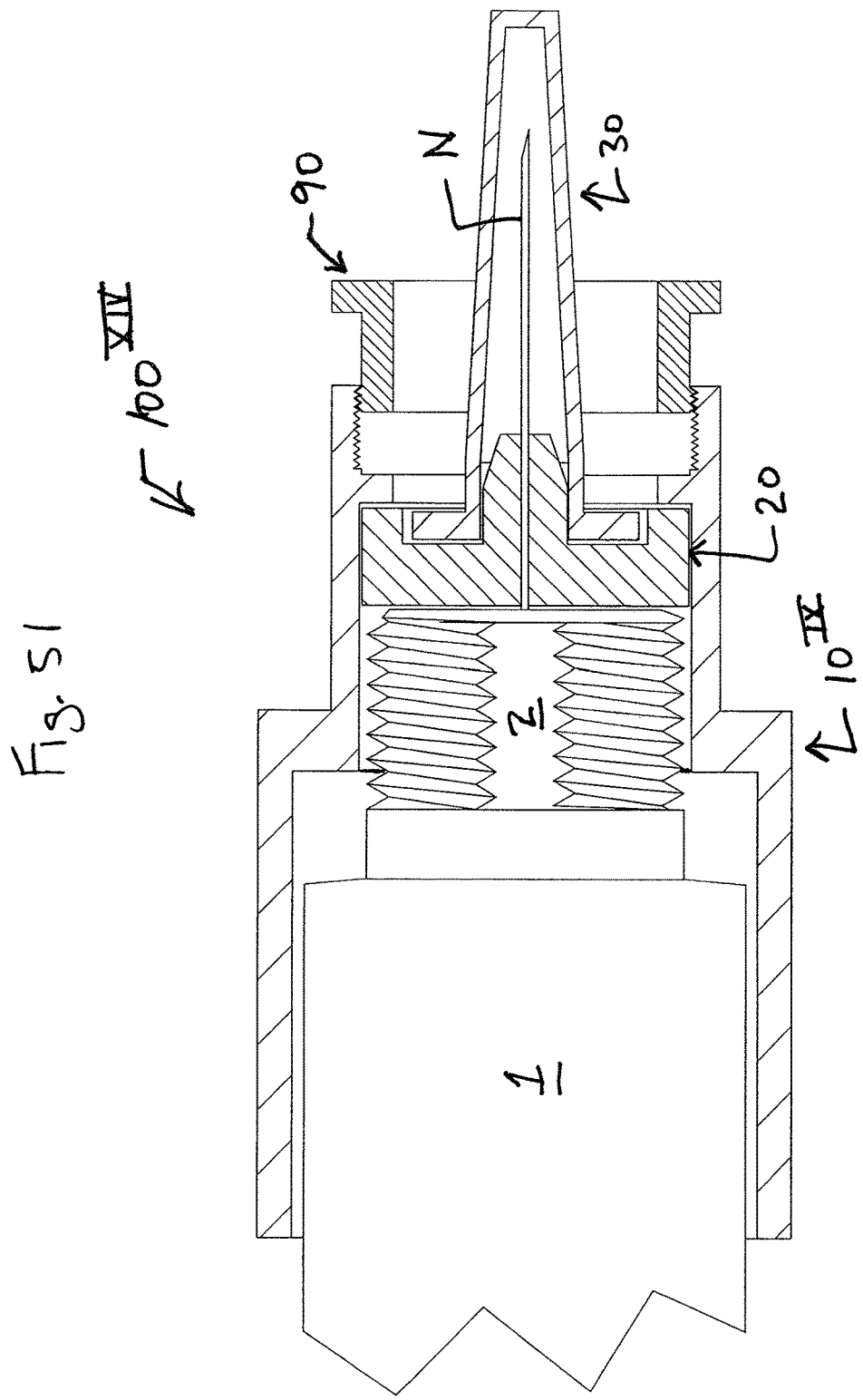

PEN NEEDLE TIP AND METHOD OF MAKING AND USING THE SAME

CROSS-REFERENCE TO RELATED APPLICATIONS

The instant application is a US non-provisional application that is based on and claims the benefit of U.S. provisional application No. 62/023,456, filed Jul. 11, 2014, the disclosure of which is hereby expressly incorporated by reference thereto in its entirety.

BACKGROUND OF THE INVENTION

1. Field of the Invention

This invention relates generally to pen needles, e.g., pen needles used with pre-loaded syringes, such are utilized for injection of medicament into the body tissues of human and animal patients. More specifically, this invention relates to a pen needle or pen needle tip or pen needle tip system which can be prevented from reuse.

2. Discussion of Background Information

U.S. Pat. No. 7,871,397, the disclosure of which is hereby expressly incorporated by reference in its entirety, discloses various embodiments of a pen needle tip and teaches one or more embodiments that utilize a mechanism for preventing reuse of the pen needle.

Although the invention disclosed in U.S. Pat. No. 7,871,397 is believed to a significant improvement over the prior art, it is desirable to provide a pen needle system which is even safer and/or easier to use and/or has more advantageous features or benefits.

SUMMARY OF THE INVENTION

According to one non-limiting embodiment of the invention, there is provided a pen needle or pen needle tip assembly that utilizes one or more features shown in the drawings.

According to another non-limiting embodiment of the invention, there is provided a pen needle tip for a pen needle wherein the pen needle tip assembly is configured to prevent it from being re-used.

According to another non-limiting embodiment of the invention, there is provided a needle tip for a device such as, e.g., a pre-loaded syringe, which can be used only once, i.e., single-use tips, and/or to tips which include one or more mechanisms for preventing the user from being pricked when handling the tip.

According to another non-limiting embodiment of the invention there is provided a needle tip assembly for a pre-loaded syringe or a pen needle injection device, wherein the needle tip assembly comprises a needle mounted to a needle support and comprising a first puncturing end projecting from a front side of the needle support and a second puncturing end projecting from a rear side of the needle support. A body is sized and configured to receive therein the needle support and the needle. The body comprises a front portion, a rear portion, and an overall axial length that is greater than an axial length of the needle. Prior to the needle tip assembly being in an installed condition on the pre-loaded syringe or the pen needle injection device, each of the front portion covers the first puncturing end and the rear portion covers the second puncturing end. Prior to removal from the pre-loaded syringe or the pen needle injection device, the body is at least axially movably relative to the needle support to a position the front portion covers the first puncturing end.

According to a non-limiting embodiment of the invention, the needle tip assembly is a single-use needle tip assembly.

According to a non-limiting embodiment of the invention, the body is a one-piece body.

According to a non-limiting embodiment of the invention, the needle support is a one-piece body.

According to a non-limiting embodiment of the invention, the needle support is generally disk-shaped.

According to a non-limiting embodiment of the invention, the needle support is a synthetic resin member.

According to a non-limiting embodiment of the invention, the needle is a double-ended hollow metal needle having similarly shaped opposite puncturing ends.

According to a non-limiting embodiment of the invention, the needle tip assembly may further comprise a packaging cover sized and configured to contain therein the body, needle support and the needle in a prior-use configuration.

According to a non-limiting embodiment of the invention, the needle tip assembly may further comprise a packaging cover and removable pull-tab arrangement adapted to store therein the body, needle support and the needle in a sterile condition.

According to a non-limiting embodiment of the invention, there is provided a needle tip assembly for a pre-loaded syringe or a pen needle injection device, wherein the needle tip assembly comprises a needle mounted to a needle support and comprising a first puncturing end projecting from a front side of the needle support and a second puncturing end projecting from a rear side of the needle support. A body is sized and configured to receive therein the needle support and comprises a front portion, a rear portion, and an overall axial length that is greater than an axial length of the needle. Prior to the needle tip assembly being installed on the pre-loaded syringe or the pen needle injection device, each of the front portion covers the first puncturing end and the rear portion covers the second puncturing end. After injection and while installed on the pre-loaded syringe or the pen needle injection device, the body is at least axially movably relative to the needle support to a position wherein the front portion covers the first puncturing end.

According to a non-limiting embodiment of the invention, the needle tip assembly is a single-use needle tip assembly.

According to a non-limiting embodiment of the invention, the body is a one-piece body having a generally circular cross-section.

According to a non-limiting embodiment of the invention, the needle support is at least one of a one-piece body non-removably coupled to a central area of the needle and generally disk-shaped and has a circular cross-section.

According to a non-limiting embodiment of the invention, the rear portion of the body always covers the second puncturing end and the front portion of the body is movable between an initial position covering the first puncturing end, a retracted position exposing the first puncturing end and a post-use position covering the first puncturing end.

According to a non-limiting embodiment of the invention, the needle support comprises at least one locking element.

According to a non-limiting embodiment of the invention, the needle tip assembly may further comprise a packaging cover sized and configured to contain therein the body, needle support and the needle in a prior-use configuration.

According to a non-limiting embodiment of the invention, the needle tip assembly may further comprise a packaging cover and removable pull-tab arrangement adapted to store therein the body, needle support and the needle in a sterile condition.

According to a non-limiting embodiment of the invention, the needle support and the body are capable of being in locking engagement with one another so as to prevent re-use of the needle tip assembly.

According to a non-limiting embodiment of the invention, the needle tip assembly may further comprise at least one retaining mechanism adapted to limit axial movement of the body relative to the needle support when the needle tip assembly is in an installed condition.

According to a non-limiting embodiment of the invention, there is provided a single-use needle tip assembly for a pre-loaded syringe or a pen needle injection device, wherein the needle tip assembly comprises a needle mounted to a needle support and comprising a first puncturing end projecting from a front side of the needle support and a second puncturing end projecting from a rear side of the needle support. A body is sized and configured to receive therein the needle support and comprises a front portion, a rear portion and an overall axial length that is greater than an axial length of the needle. Prior to the needle tip assembly being installed on the pre-loaded syringe or the pen needle injection device, each of the front portion covers the first puncturing end and the rear portion covers the second puncturing end. Prior to the needle tip assembly being removed from the pre-loaded syringe or the pen needle injection device, each of the front portion covers the first puncturing end and the rear portion covers the second puncturing end. The body moves relative to the needle support in one direction during installation and moves relative to the needle support in another direction during removal.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

At least FIGS. 1-13 are intended to show basic features and functioning of non-limiting embodiments and, for purposes of illustration, do not necessarily show features which would or could be utilized in commercial embodiments.

FIG. 1 shows a side view of an inventive needle tip assembly about to be installed onto a pen injector or pre-loaded syringe. The pen needle tip is shown in cross-section with the exception of the needle;

FIG. 2 shows a partially installed state of the tip of FIG. 1. In this position, the second puncturing end projecting from a rear side of the needle support has penetrated the puncturable/resealable septum of the pre-loaded syringe;

FIG. 3 shows a nearly fully installed state of the tip of FIG. 1. In this position, the body and pre-loaded syringe are moved relative to one another and this results in or causes the needle support to move within the body;

FIG. 4 shows the needle tip assembly of FIG. 1 in an installed and ready to inject condition. In this position, the needle support has moved to a final forward position relative to the body and the first puncturing end of the needle projects out from the front end of the body;

FIG. 5 shows the configuration of FIG. 4 after injection or use and as the used tip assembly is caused to be removed;

FIG. 6 shows the configuration of FIG. 5 after the used tip assembly is fully removed;

FIG. 7 shows another non-limiting embodiment and in an installed position;

FIG. 8 shows the non-limiting embodiment of FIG. 7 as a needle tip cover is being removed to expose the skin puncturing needle;

FIG. 9 shows another non-limiting embodiment and in an uninstalled position;

FIG. 10 shows the non-limiting embodiment of FIG. 9 in an installed position and prior to the needle tip cover is being removed to expose the skin puncturing needle;

FIG. 11 shows the non-limiting embodiment of FIG. 10 as a needle tip cover is being removed to expose the skin puncturing needle;

FIG. 12 shows another non-limiting embodiment and in an uninstalled position;

FIG. 13 shows the non-limiting embodiment of FIG. 12 in an installed position or state and a ready to inject position;

FIG. 14 shows another non-limiting embodiment and in an uninstalled position;

FIGS. 15-19 show views of the components used in the embodiment shown in FIG. 14;

FIG. 20 shows another non-limiting embodiment and in an uninstalled position;

FIGS. 21-23 show views of the components used in the embodiment shown in FIG. 20;

FIGS. 30-32 show views of the components used in the embodiment shown in FIG. 27;

FIG. 33 shows another non-limiting embodiment installed and in a puncturing or ready-to-puncture position;

FIG. 34 shows an embodiment similar to that of FIG. 33 in an installed and prior to puncturing position and utilizing an outer cover;

FIG. 35 shows another non-limiting embodiment installed and in a puncturing or ready-to-puncture position;

FIG. 36 shows an enlarged view of a portion of FIG. 35;

FIG. 37 shows another non-limiting embodiment and in an about-to-be-installed position;

FIG. 38 shows the embodiment of FIG. 37 in an installed and prior to puncturing position;

FIG. 39 shows the embodiment of FIG. 37 in a removed and post-use position or state;

FIG. 51 shows an embodiment similar to that of FIG. 7 but modified to include a depth of penetration adjustment system/arrangement.

DETAILED DESCRIPTION OF THE INVENTION

Figure 1:
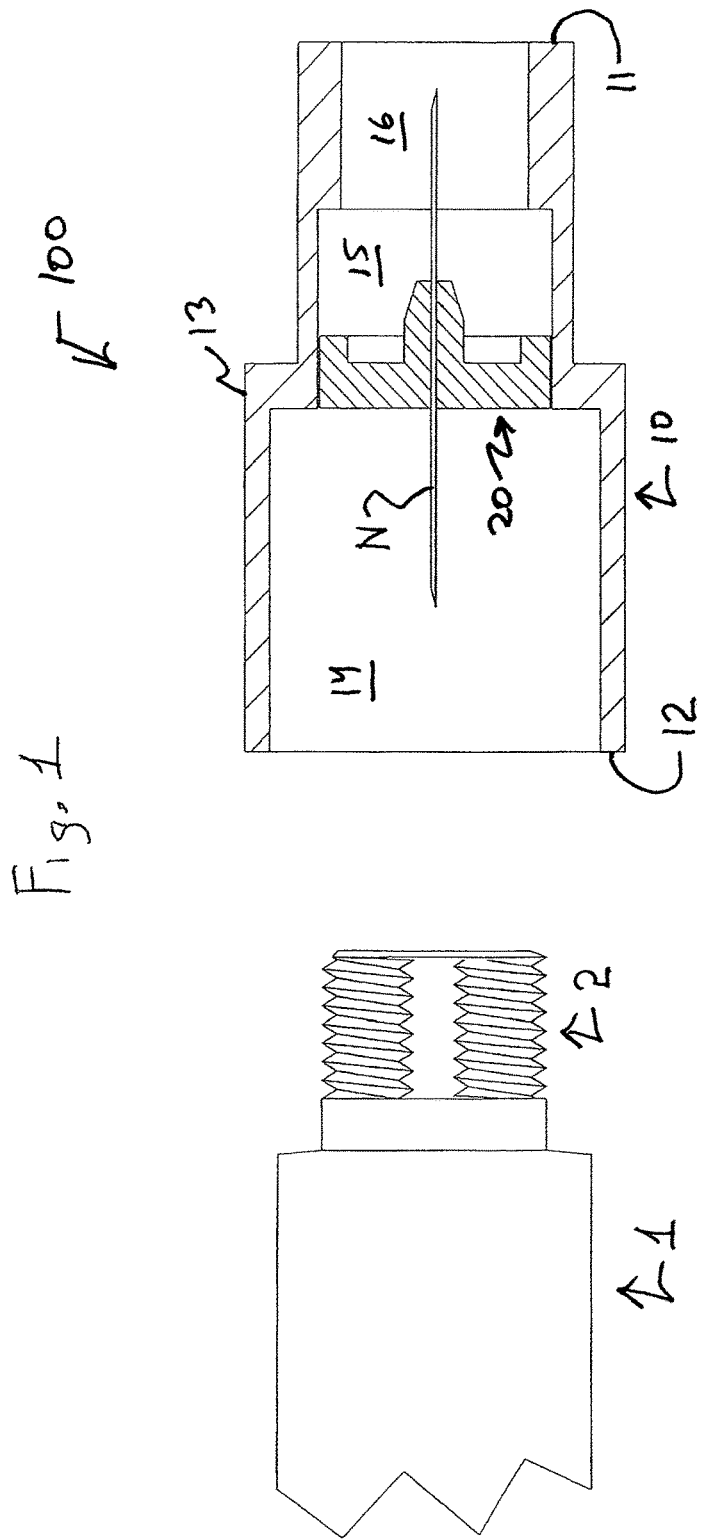

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 1-6 show one non-limiting embodiment of a pen needle, pen needle tip or pen needle assembly 100. The pen needle 100 includes the following main components: a body 10 which can be a one-piece body, a needle support 20 which can be a one-piece member, and a double-ended hollow needle N.

As can be appreciated from FIGS. 1-6, the pen needle 100 can be installed on and removed from a pre-loaded syringe or injection device 1 essentially in a conventional manner. Typically, a conventional pre-loaded syringe has a threaded front portion 2 to which the pen needle is threaded onto. While the instant invention can utilize a thread or one or more thread segments on the body 10 to allow the pen needle 100 to be threaded on in the conventional manner, a non-limiting advantage if the invention is that this not necessarily required. Instead, a user can simply grip the body 10 and slide it onto the end 2 of syringe 1 in the manner illustrated in FIGS. 1-4, i.e., without requiring threading-on or rotation. Removal would occur in the manner illustrated in FIGS. 5 and 6, i.e., by simply sliding it off axially and without any rotation being required.

Again referring to FIG. 1, the body 10 of the pen needle 100 has a front end 11 which is annular, a rear end 12 which is also annular, a main sidewall portion 13, a rear internal generally cylindrical space 14 sized and configured to receive or slide over the end 2 of the device 1. A middle or needle support receiving internal generally cylindrical space 15 is sized and configured to receive therein the end 2 of the device 1 and also to allow axial sliding movement therein of the needle support 20. A front generally cylindrical internal space 16 is sized and configured to receive therein a skin puncturing or front end of the needle N and also functions to protect the front end of the needle N when the pen needle 100 is in an initial or original position (see FIG. 1) and in the post-use or used position (see FIG. 6). As a result of this configuration, the needle N has both ends safely covered in these positions while at the same time the pen needle 100 is of simpler construction. The pen needle 100 can also be made for lower relative cost compared to pen needles utilizing one or more safety covers or members.

Figure 2:
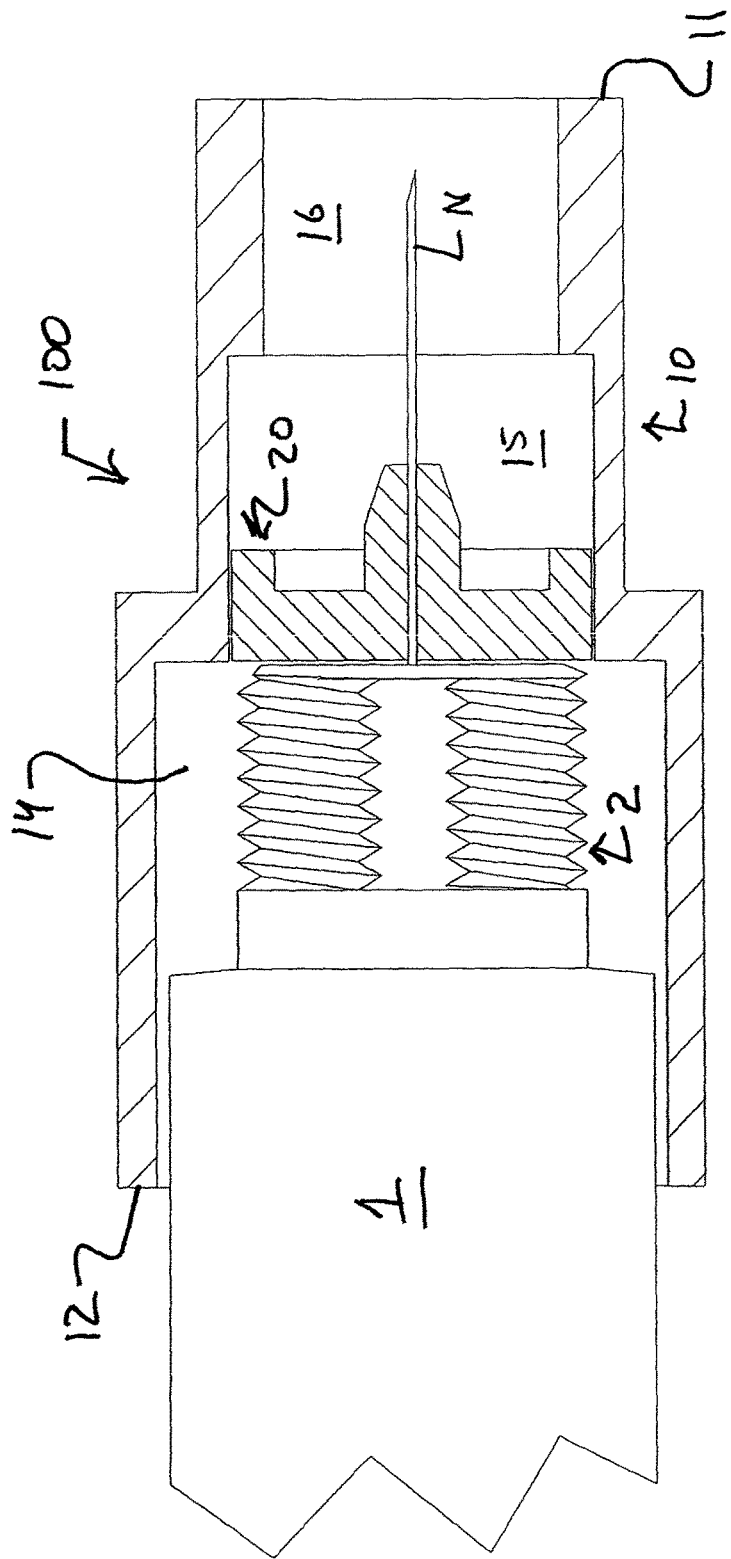
Figure 3:
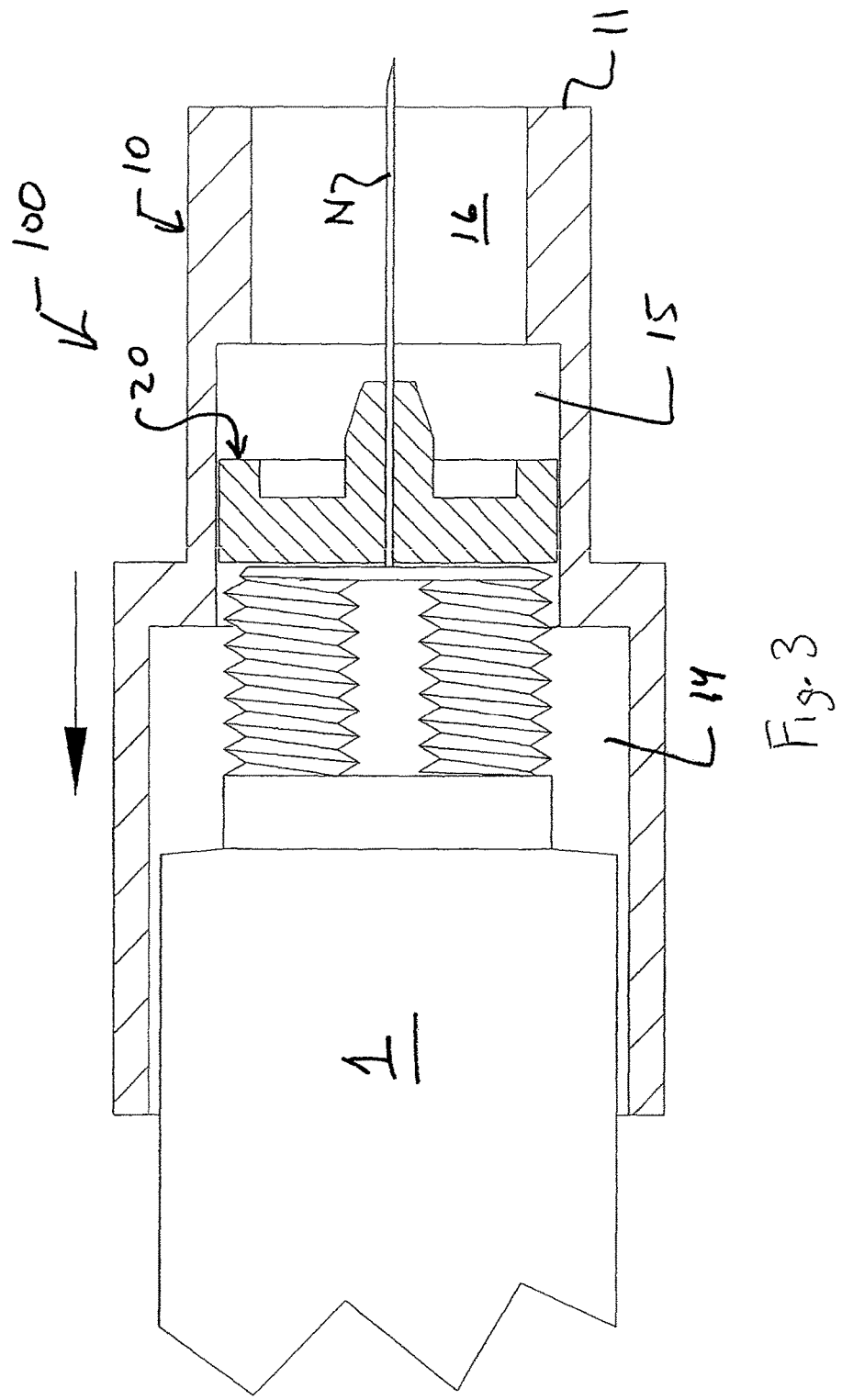
Figure 4:
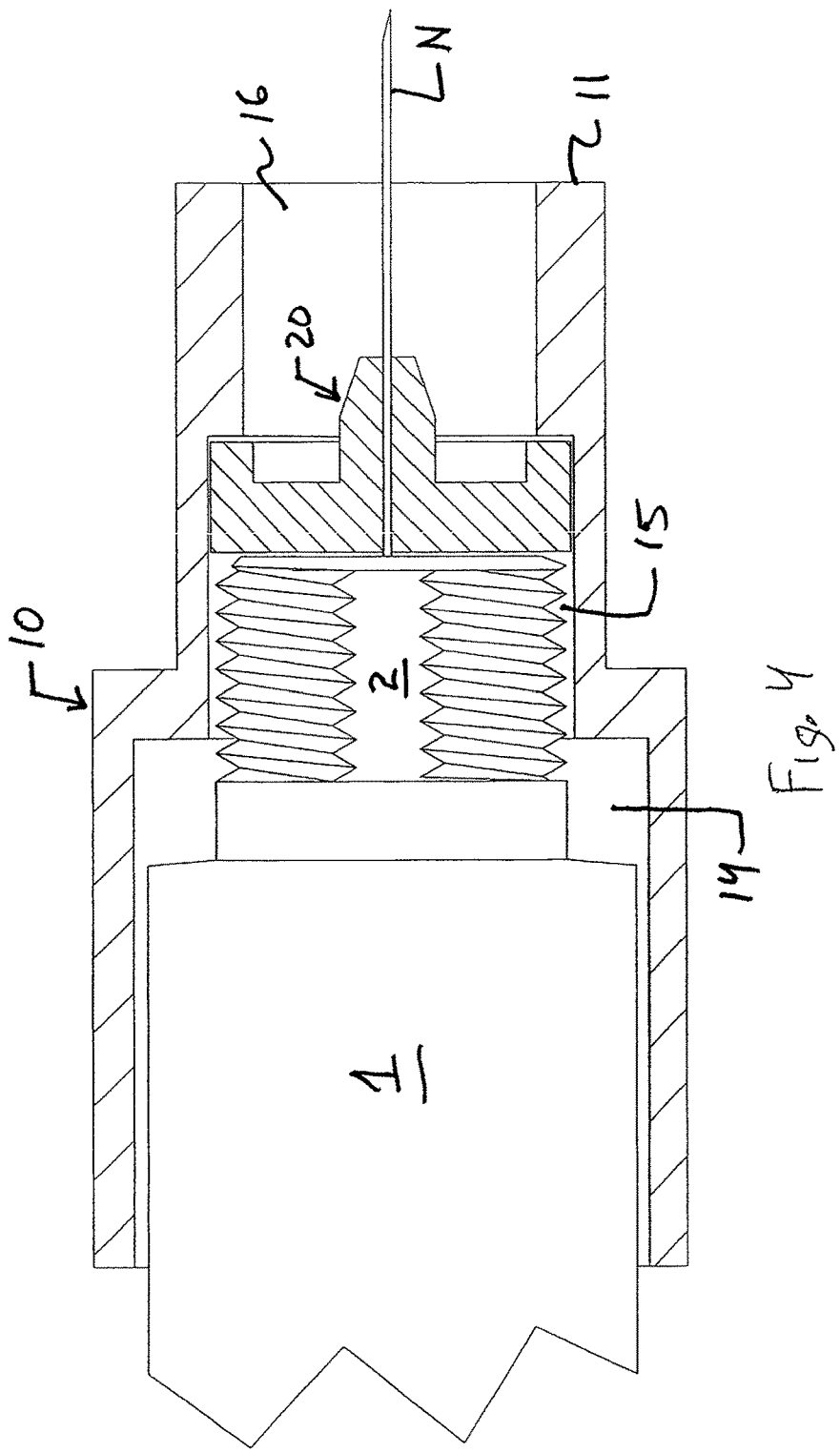

Referring now to FIGS. 1-4, one can appreciate that installation and use of the pen needle 100 can occur by a user gripping the body 10 and either sliding the end 2 into the space 14 or sliding the body 10 over the end 2. During this axial installation movement, the rear puncturing end of the needle N will puncture the septum (not shown) of the end 2. As this movement continues, the end 2 will eventually make contact with the needle support 20, as shown in FIG. 2. At this point, it should be apparent, neither the rear or septum puncturing end nor the front or skin puncturing end of the needle N are exposed. As in the case of FIG. 1, both ends remain covered by the body 10 and the user is protected from being punctured thereby. Moreover, the rear end 12 is disposed over a portion of the syringe 1 located behind the end 2 and the end 2 is disposed inside the space 14. As this movement continues, the end 2 will push the needle support 20 and cause it to move axially relative to the body 10 (or vice versa) until the support 20 contacts a shoulder located at a front side of the space 15, as shown in FIGS. 3 and 4. At this point, it should be apparent that the front or skin puncturing end of the needle N is exposed and in the ready-to-puncture position. A use can now puncture the skin and administer an appropriate dosage of medicine.

Of course, in this example, the pen needle 100 remains installed on the device 1 owing mainly to the frictional engagement between the septum and the rear end of the needle N. As such, rather than place the pen needle 100 in the position shown in FIG. 4 prior to skin injection, the user can instead place the pen needle 100 in the position shown in FIG. 2, and then force the end 11 against the skin to both cause the movement of FIGS. 3 and 4 and simultaneously cause skin puncturing.

Figure 5:
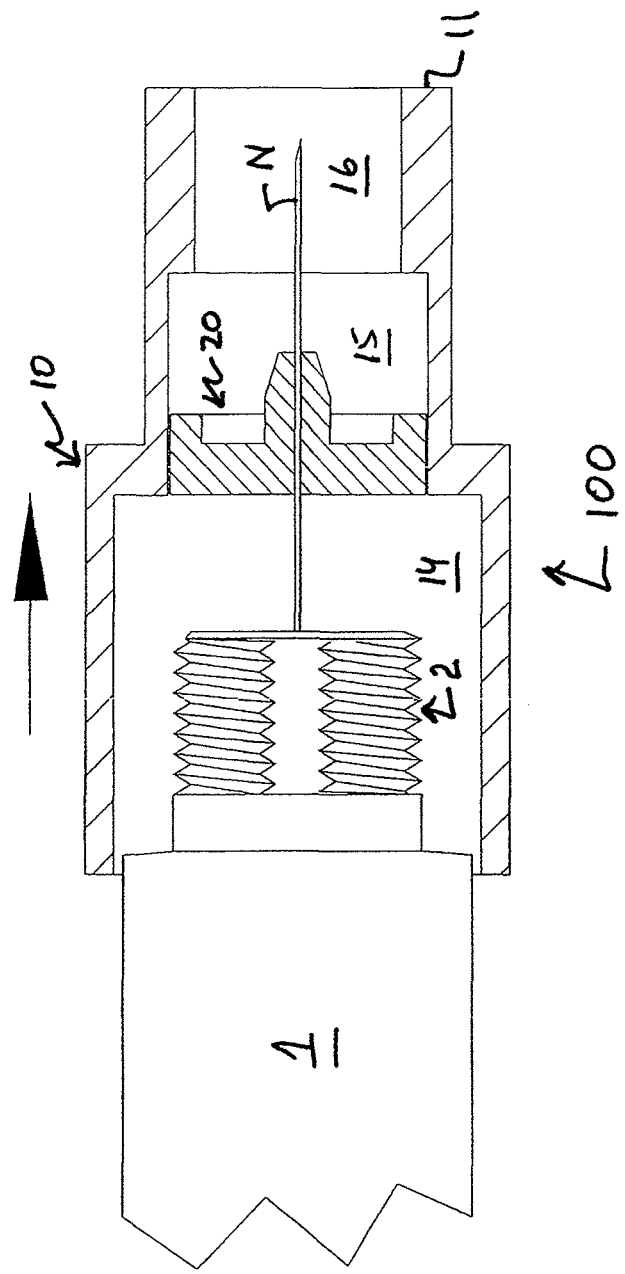

As is illustrated in FIGS. 5 and 6, the pen needle 100 can be removed from the device 1 after skin injection by simply gripping the body 10 and pulling it off the device 1. During this movement, the frictional engagement between the septum and the rear end of the needle N is sufficient to allow the needle support 20 to be pulled back until the skin puncturing end of the needle N is back safely disposed within the space 14. Although not shown, the pen needle 100 can include a mechanism to prevent the support 20 from moving back further into the body 10 to the point where the rear end of the needle N is no longer safely disposed within the space 14. After being fully removed, as shown in FIG. 6, the used pen needle 100 can again be safely handled and now be safely discarded in an appropriate container, e.g., a sharps container.

FIGS. 7 and 8 show another non-limiting embodiment of a pen needle, pen needle tip or pen needle assembly 100'. The pen needle 100' includes the following main components similar to the previous embodiment: a body 10 which can be a one-piece body, a needle support 20 which can be a one-piece member, and a double-ended hollow needle N. In addition, the pen needle 100' includes a needle cap 30 which can be a one-piece member. The advantage of this embodiment can be seen in FIG. 7 which shows how the skin puncturing end of the needle N remains covered, i.e., via a needle cap 30, even when the pen needle is fully installed on the device 1. When the user wishes to proceed with skin injection, the user need only remove or pull off the needle cap 30 as shown in FIG. 8. This exposes the skin puncturing end of the needle N. Although not shown, an overall length of the cap 30 can be such that when the pen needle 100' is in a prior use position (comparable to FIG. 1), the forward end of the cap 30 can be essentially flush with or project only slightly past the end 11 so that the user cannot readily grip and remove the same prematurely. In the installed position shown in FIG. 7, the forward end of the cap 30 can project past the end 11 more significantly. This allows for it to be more easily gripped for removal. Moreover, with such an arrangement, a user is provided with a visual indication as to whether the pen needle 100' is in a prior-use position or a ready-to-use position. After injection, the cap 30 can also be immediately re-installed to make removal of the pen needle 100' even more safely accomplished. With the exception of re-installing the cap 30, removal of the pen needle 100' can otherwise occur in the same way as shown in FIGS. 5 and 6.

FIGS. 9-11 show another non-limiting embodiment of a pen needle, pen needle tip or pen needle assembly 100". The pen needle 100" includes the following main components similar to the previous embodiment: a body 10 which can be a one-piece body, a needle support 20 which can be a one-piece member, a double-ended hollow needle N and also a needle cap 30 which can be a one-piece member. This embodiment additional includes an alignment and/or spacer ring 40. The advantage of this embodiment can be seen when comparing the FIGS. 9 and 10 which shows how the ring 40 helps to centrally or coaxially align the section 2 with the needle N and space 15 as the pen needle is fully installed on the device 1. As should be apparent, if one were to make the ring 40 so as to have a greater axial thickness (not shown), the result would be that the skin puncturing end of the needle N would protrude past the end 11 by a lesser amount. This is because the shoulder SH would be spaced by a greater amount from the shoulder SHF of the body 10 located at the front end of the space 14. The ring 40 shown in FIGS. 9 and 10 is not so axially thick as to prevent the support 20 from moving to a point where the support 20 contacts the shoulder between the space 15 and the space 16. However, an axially thicker ring 40 could be sufficiently axially thick as to prevent the support 20 from moving to a point where the support 20 contacts the shoulder between the space 15 and the space 16. By providing a ring 40 with a particular axially thickness, one can provide the pen needle 100" with a predetermined penetration depth. Moreover, the pen needle 100" can be packaged with a number of different axial thickness rings, e.g., 2, 3, 4, 5, etc., which would allow the user to select the desired ring for a desire skin puncturing depth. Each ring can be conveniently made of a different color or marked with indicia indicating the puncturing depth. The pen needle 100" shown in FIGS. 9 and 10 can otherwise function in a manner comparable to that of one or more of the previously described embodiment. One exception is that in this embodiment, once the pen needle 100" is removed (not shown), the ring 40 could remain adjacent the shoulder SHF as shown in FIG. 10. Since the ring 40 would not in the further back position shown in FIG. 9 after use, the user would have a visual indication that the pen needle 100" has already been used and should be discarded. To facilitate this option and also prevent the ring 40 from falling out of the space 14, the ring 40 can be a split ring (biasing the ring 40 into slight frictional contact with the wall surrounding the space 14) or can be made to snugly or slightly tightly fit within the space 14 to ensure that it remains in place in the space 14 unless it is moved axially.

FIGS. 12 and 13 show a variation of the previous non-limiting embodiment in that pen needle assembly 100" need to not utilize a needle cap 30. As should be apparent, the skin puncturing end of the needle N remains covered when in the initial unused position. Although not shown, the skin puncturing end of the needle N would also remain covered when in the post use position.

FIGS. 14-19 show another non-limiting embodiment of a pen needle, pen needle tip or pen needle assembly 100'. The pen needle 100' includes the following main components similar to the previous embodiment: a body 10' which can be a one-piece body, a needle support 20' which can be a one-piece member, and a double-ended hollow needle N. This embodiment additional includes a system or arrangement of limiting the axial movement of the support 20'. The advantage of this embodiment is that it includes an integrally formed system for prevent the support 20" from being removed and/or moved back out of the space 15'. Thus, after injection and when the pen needle 100' is being removed from the device 1, the support 20' will move back axially only up to a point, i.e., essentially the same point or position that it had when the pen needle 100' was not yet used or installed. After this point, the septum of the section 2 will necessarily allow removal the septum puncturing end with the needle N until the pen needle 100' is fully removed. As should be apparent from FIGS. 14-19, the system is a movement limiting system that utilizes retaining projections RP which move within guide recesses GR. The forward tapered ends of the retaining projections RP allow for easy insertion and installation of the support 20' into the space 15' whereas the straight back surfaces of the projections RP prevent easy remove of the support 20' once installed. The same contact that would prevent removal of the support 20' also serves to limit rearward movement of the support 20' relative to the body 10' during removal of the pen needle 100' from the device 1. Thus, the pen needle 100' would have the configuration shown in FIG. 14 before it is used or installed and also after it is removed from the device 1. In both of these positions, both the front and rear puncturing ends of the needle N are safely covered by respective front and back portions of the body 10'. Although two projections RP and two guide recesses GR are shown and are arranged opposite one another (spaced 180 degrees apart from one another), the number of recesses and projections can be, for example, 3, 4, 5 or more. Moreover, although the support 20' includes the projections GR and the body 10" includes the recesses GR, these could be switched (not shown) so that the support 20' includes recesses and the body 10" includes projections.

FIGS. 18 and 19 show details of the support 20' which includes a front end 21' and a rear end 22' arranged on opposite or front and back sides of an outer cylindrical body 23'. A hub 24' is arranged on the front side and serves to centrally align, retain and secure the needle N to the support 20'. As should be apparent from FIGS. 18 and 19, the projections RP are integrally formed on a thinned walled portion behind the front end 21' and formed by an annular recessed area 25'. This allows the projections RP to deflect inwardly slightly during installation of the support 20' into the body 10'. One way to efficiently manufacture the support 20" is to injection mold the same around the needle N using the process known as "insert molding."

FIGS. 20-23 show another non-limiting embodiment of a pen needle, pen needle tip or pen needle assembly $100^{IV}$. The pen needle $100^{IV}$ includes the following main components similar to the previous embodiment: a body 10" which can be a one-piece body, a needle support 20 which can be a one-piece member, and a double-ended hollow needle N. This embodiment also includes a system or arrangement of limiting the axial movement of the support 20. The advantage of this embodiment is that it includes a non-integrally formed system for prevent the support 20 from being removed and/or moved back out of the space 15". Thus, after injection and when the pen needle $100^{IV}$ is being removed from the device 1, the support 20 will move back axially only up to a point, i.e., essentially the same point or position that it had when the pen needle $100^{IV}$ was not yet used or installed. After this point, the septum of the section 2 will necessarily allow removal the septum puncturing end with the needle N until the pen needle $100^{IV}$ is fully removed. As should be apparent from FIGS. 20-23, the system is a movement limiting system that utilizes a ring or washer 50 which is seated in and axially retained in a retaining recess 17". The washer 50 can be split, is desired, to allow for easy insertion and installation of the recess 17". The washer 50 has an inside diameter opening that is smaller in diameter than an outer diameter of the support 20 and this functions to prevent the support 20 from moving back past the position shown in FIG. 20. However, the inside opening of the washer 50 is still larger than the section 2 and allows the section 2 to pass there through in order to make contact with the support 20 and exert a pushing force against the same to cause it to move within the space 15". The support 20 will make contact with the washer 50 when the support 20 is caused to move backward during removal of the pen needle $100^{IV}$ and thus has a backward axial movement limited thereby. This contact would prevent removal of the support 20 and also serves to limit rearward movement of the support 20 relative to the body 10" during removal of the pen needle $100^{IV}$ from the device 1. Thus, the pen needle $100^{IV}$ would have the configuration shown in FIG. 20 before it is used or installed and also after it is removed from the device 1. In both of these positions, both the front and rear puncturing ends of the needle N are safely covered by respective front and back portions of the body 10". Unlike the previous embodiment utilizing movement limiting projections and recesses, this embodiment would allow for some rotation movement of the support 20 relative to the body 10".

Figure 24:
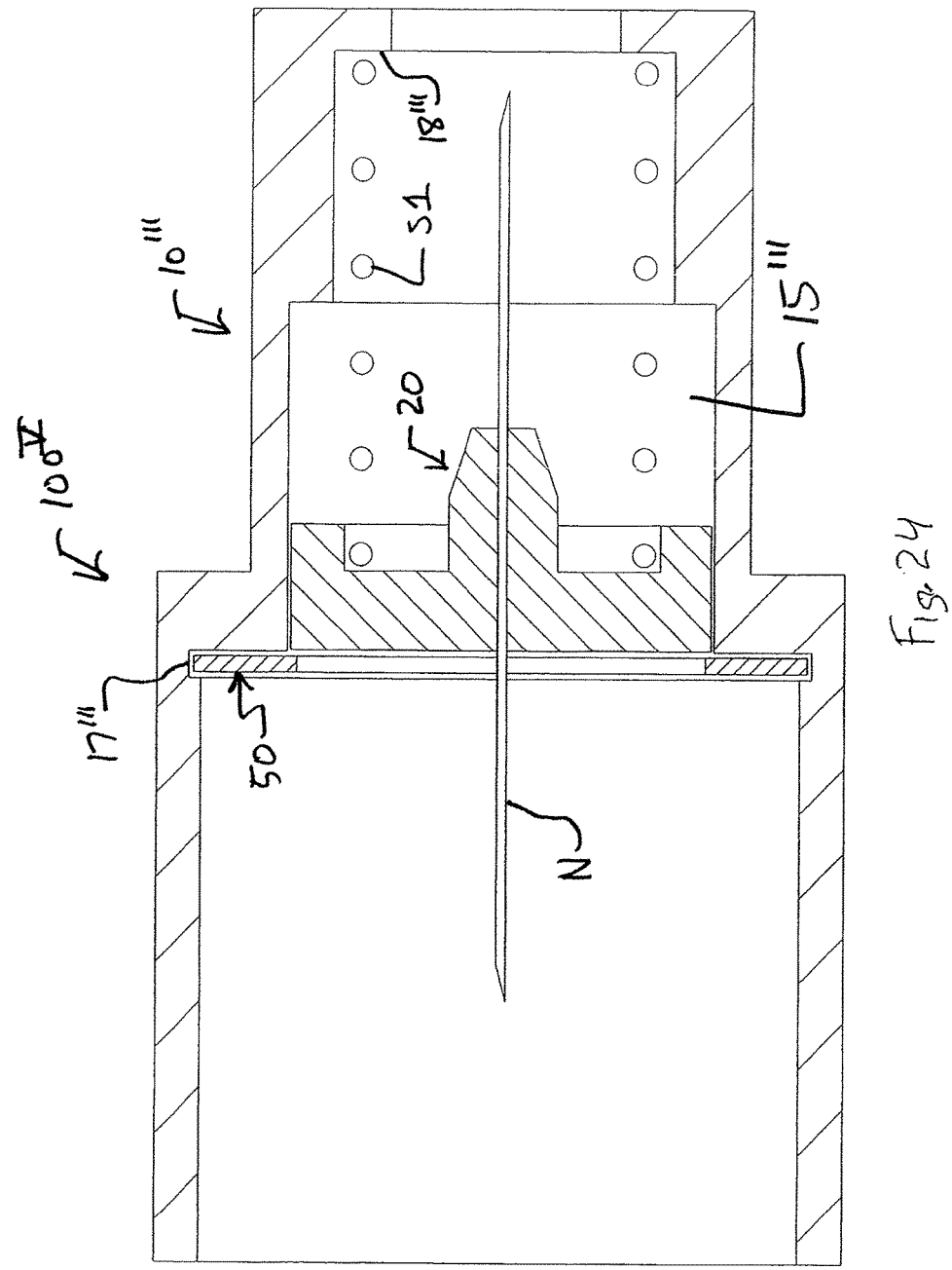
FIG. 24 shows another non-limiting embodiment and in an uninstalled position.

FIG. 24 shows another non-limiting embodiment of a pen needle, pen needle tip or pen needle assembly $100^V$. The pen needle $100^V$ includes the following main components similar to the previous embodiment: a body 10''' which can be a one-piece body, a needle support 20 which can be a one-piece member, a double-ended hollow needle N and a system or arrangement of limiting the axial movement of the support 20 having the form of a washer 50. In addition, a compression spring S1 is used to bias the support 20 toward an original position shown in FIG. 24. The advantage of this embodiment is that a looser fit can be provided between the support 20 and the space 15". The spring S1 has a forward end that abuts a shoulder 18''' and a rear end that contacts the support 20 and is slightly compressed in order to force the support 20 into contact with the washer 50. When the pen needle $100^V$ is installed, the support 20 is forced to move to a forward most injection position—which compresses the spring S1. During removal of the pen needle $100^V$, the spring S1 can expand axially and force the support 20 back until it again contacts the washer 50. This can provide a more full proof way to ensure that the needle N is retracted into the body 10''' during removal from the device 1.

Figure 25:
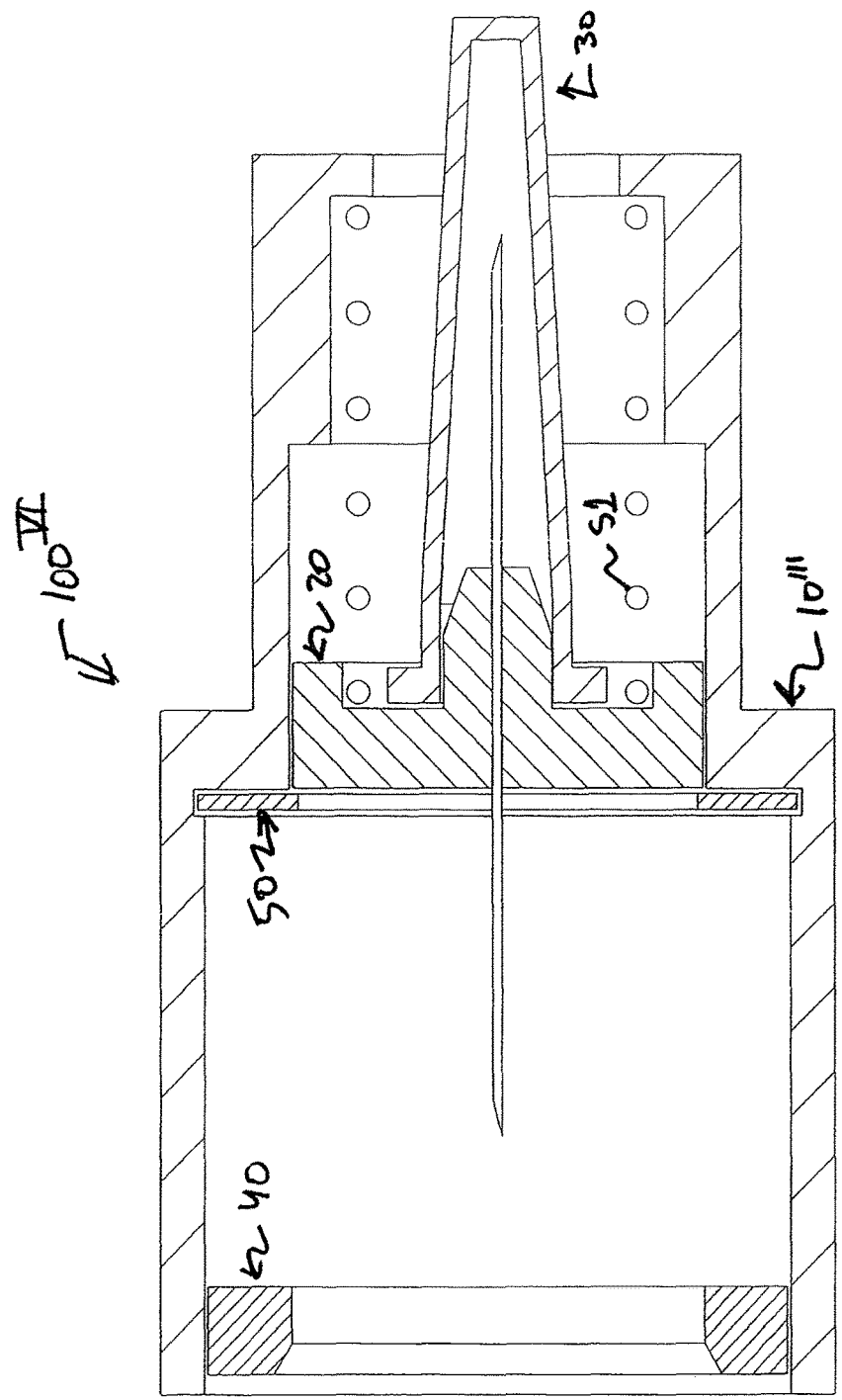
FIG. 25 shows another non-limiting embodiment and in an uninstalled position.

FIG. 25 shows another non-limiting embodiment of a pen needle, pen needle tip or pen needle assembly $100^{VI}$. The pen needle $100^{VI}$ includes the following main components similar to the previous embodiment: a body 10" which can be a one-piece body, a needle support 20 which can be a one-piece member, a double-ended hollow needle N as well as a system or arrangement of limiting the axial movement of the support 20 having the form of a washer 50 and a compression spring S1 used to bias the support 20 toward an original position shown in FIG. 25. In addition a ring 40 of the type previously described as well as a needle cap 30 of the type previously described, can be utilized. The advantages of this embodiment are comparable to that already described above.

Figure 26:
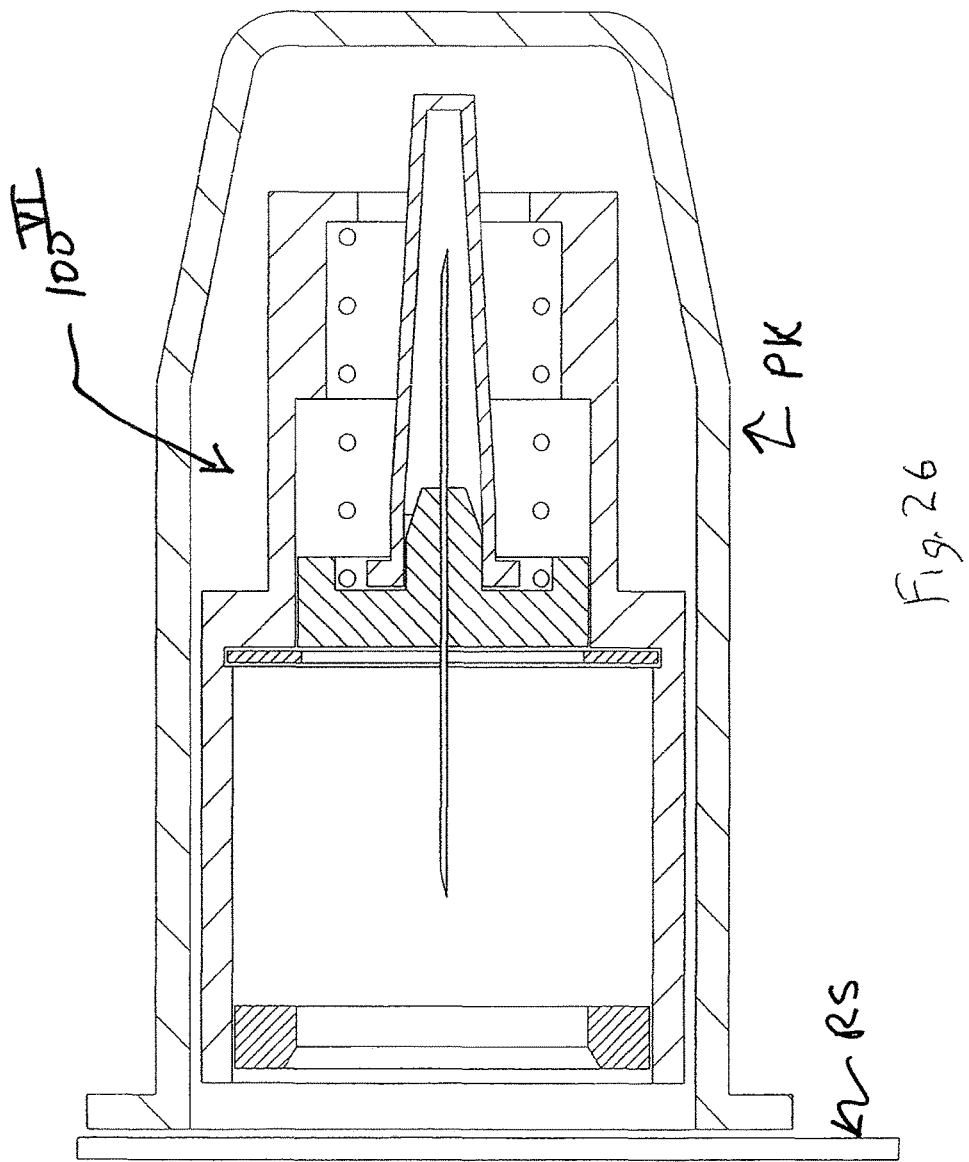
FIG. 26 a non-limiting embodiment in an uninstalled and packaged position.
Figure 27:
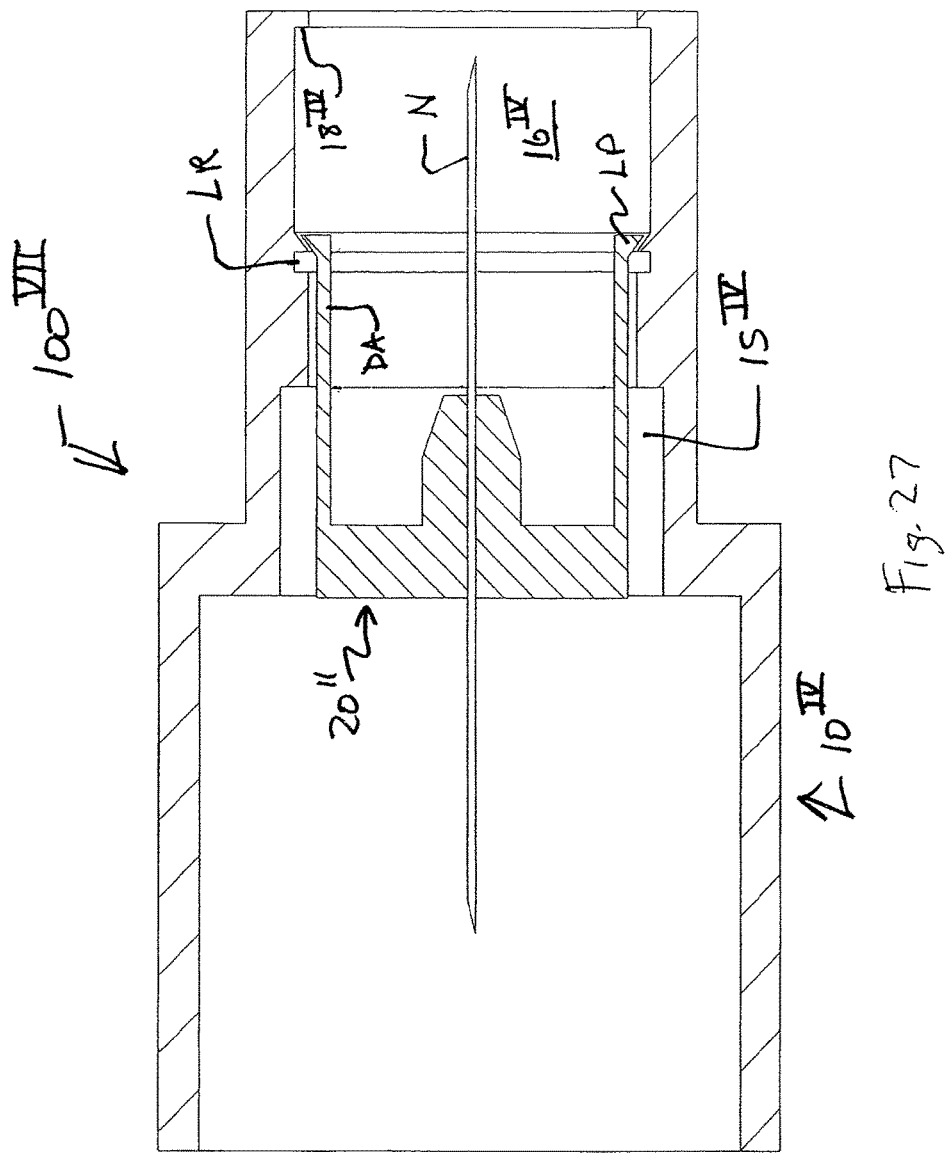
FIG. 27 shows another non-limiting embodiment and in an uninstalled and initial position.

FIG. 26 shows one non-limiting way in which one or more of the herein disclosed embodiments, such as the pen needle tip or pen needle assembly $100^{VI}$, can be packaged. The packaging preserves in a sterile manner the pen needle and includes a main packaging container or package PK as well as a removable seal RS which is adhesively secured to the package PK. A user can open the packaging by peeling off the seal RS from the package PK and removing the pen needle. Alternatively, after removing the seal RS, the use can install the pen needle on a device 1 by gripping the package PK and sliding the pen needle onto the device 1. After installation, the user can discard the package PK.

Figure 28:
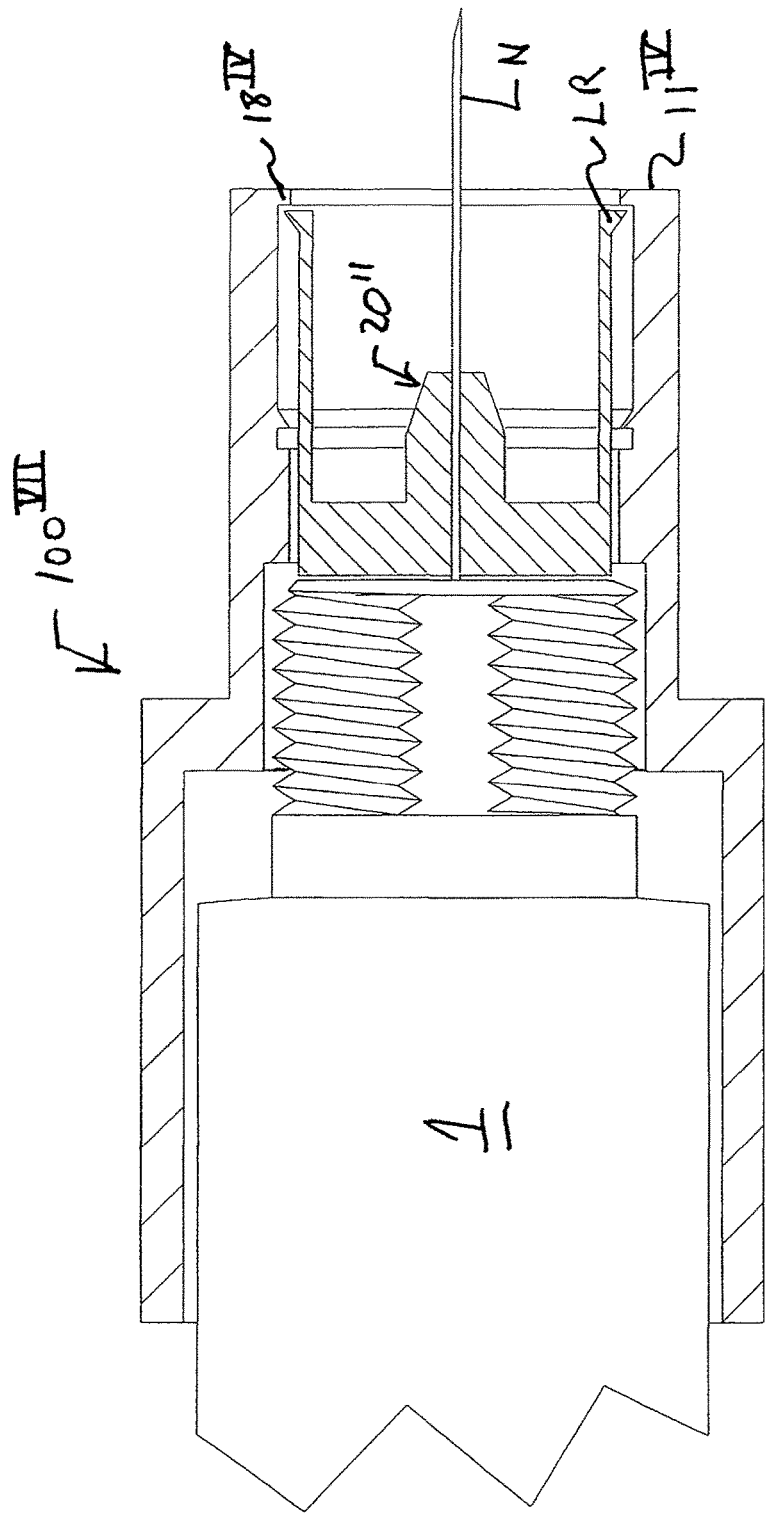
FIG. 28 shows the embodiment of FIG. 27 installed and in a puncturing position.
Figure 29:
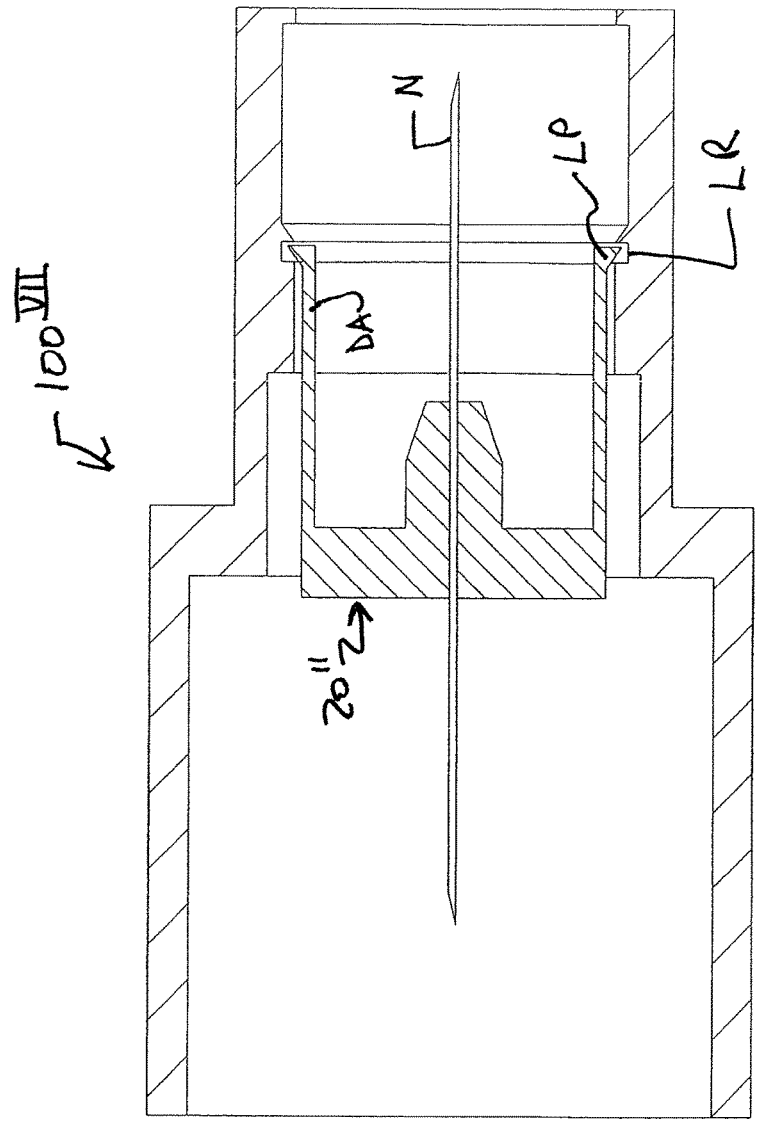
FIG. 29 shows the embodiment of FIG. 28 after being removed and a post-use locked position.
Figure 30:
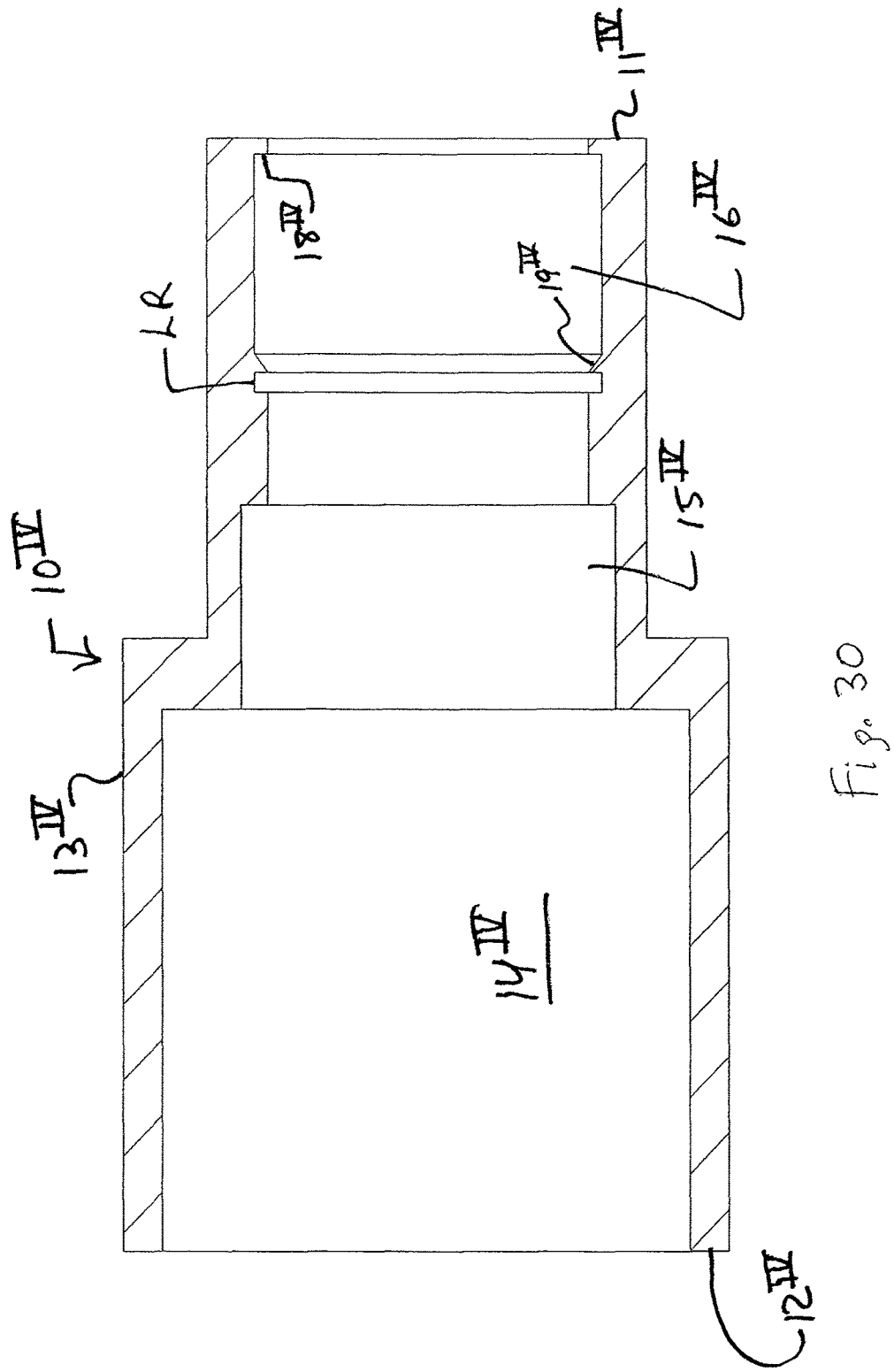
Figure 40:
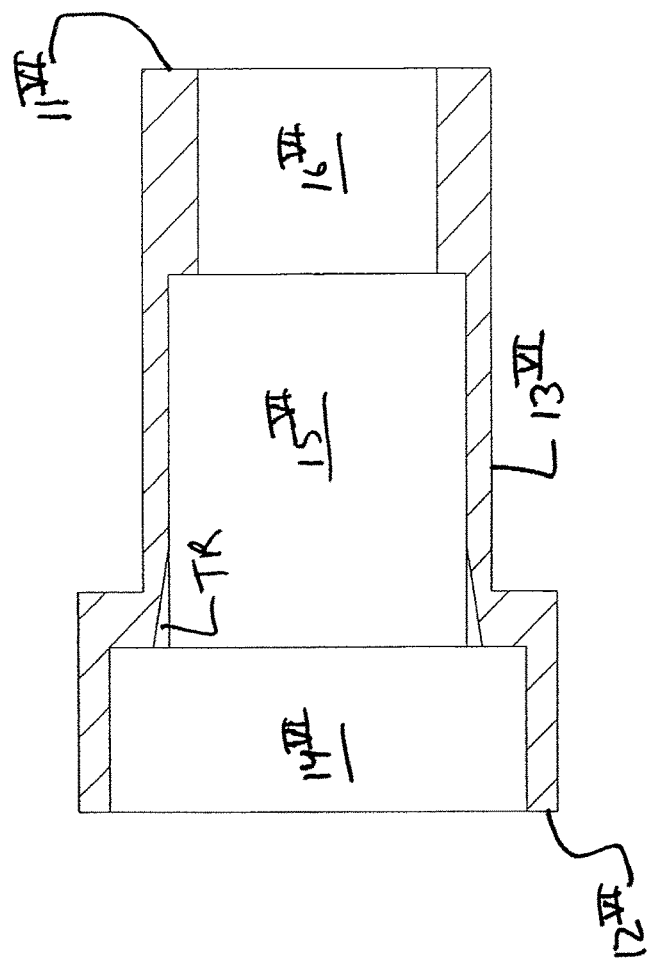
FIGS. 40-44 show views of the components used in the embodiment shown in FIG. 37.
Figure 41:
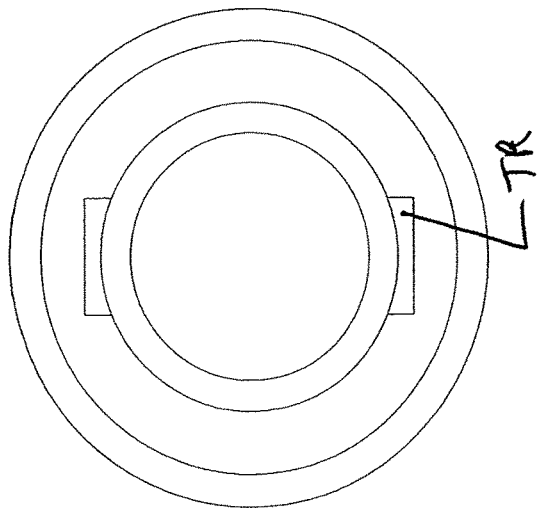

FIGS. 27-32 show another non-limiting embodiment of a pen needle, pen needle tip or pen needle assembly $100^{VII}$. The pen needle $100^{VII}$ includes the following main components similar to the previous embodiment: a body $10^{IV}$ which can be a one-piece body, a needle support 20" which can be a one-piece member, a double-ended hollow needle N and a system or arrangement of both limiting the axial movement of the support 20" and locking the same in a post-use condition. The system utilizes deflectable arms DA arranged on the support 20" which have tapered locking projections LP that can lock or snap into a locking recess LR arranged inside the body $10^{IV}$. The advantage of this embodiment is that it renders the pen needle $100^{III}$ unusable after use, i.e., it make it a single-use pen needle. Forward movement of the support 20" is limited by contact between the arms DA and the shoulder $18^{IV}$. When the pen needle $100^{VII}$ is installed, the support 20" is forced to move from the position shown in FIG. 27 to a forward most injection position shown in FIG. 28. During removal of the pen needle $100^{VII}$, the support 20" is drawn back until the locking projections LP automatically engage with the locking recess LR as shown in FIG. 28. This can provide a more full proof way to ensure that the needle N remains retracted into the body $10^{IV}$ during removal from the device 1 and after use for injection. As should be apparent from FIG. 28, the locking engagement between the locking projections LP and the locking recess LR prevent re-use of the pen needle. Should a user attempt to reinstall the pen needle in the locked position shown in FIG. 28, he or she would be unsuccessful as the locking engagement would prevent movement of the support 20" and needle N toward the puncturing position. As can be seen in FIG. 30, the locking recess LR is located behind a tapered projection $19^{IV}$ located in the space $16^{IV}$.

FIGS. 31 and 32 show details of the support 20" which includes a front end 21" and a rear end 22" arranged on opposite or front and back sides of an outer cylindrical body 23". A hub 24" is arranged on the front side and serves to centrally align, retain and secure the needle N to the support 20". As should be apparent from FIGS. 31 and 32, the projections LP are integrally formed on deflectable arms DA projecting from the front end 21" and functioning as leaf springs. This allows the projections LP to deflect inwardly slightly during installation of the support 20" into the body $10^{IV}$. One way to efficiently manufacture the support 20" is to injection mold the same around the needle N using the process known as "insert molding." Although two arms DA are shown and are arranged opposite one another (spaced 180 degrees apart from one another), the number of arms can be, for example, 3, 4, 5 or more.

FIGS. 33 and 34 show embodiments $100^{VIII}$ and $100^{IX}$ wherein instead of using plural delectable arms DA, the support 20″ has a cylindrical front section which includes a continuous locking projection. An outer cover 60 can advantageously be used to install the pen needle on the embodiment of FIG. 34. The operation or functioning would otherwise be comparable to that of the previously described embodiment.

FIG. 35 show an embodiment $100^X$ similar to that previously described except that it additionally utilizes a skin engaging cap 70 and a spring S2 which biases the support 20‴ towards an original position. The cap 70 shown in FIG. 35 is not so axially thick as to significantly change a penetration depth of the skin puncturing end of the needle N. However, an axially thicker cap 70 could be sufficiently axially thick as to reduce the penetration depth. By providing a cap 70 with a particular axially thickness, one can provide the pen needle $100^X$ with a predetermined penetration depth. Moreover, the pen needle $100^X$ can be packaged with a number of different axial thickness caps, e.g., 2, 3, 4, 5, etc., which would allow the user to select the desired ring for a desire skin puncturing depth. Each cap 70 can be conveniently made of a different color or marked with indicia indicating the puncturing depth. The pen needle $100^X$ shown in FIG. 35 can otherwise function in a manner comparable to that of one or more of the previously described embodiment.

Figure 42:
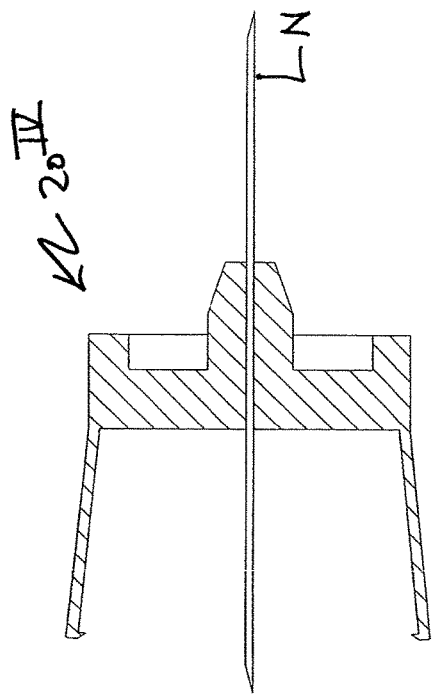
Figure 43:
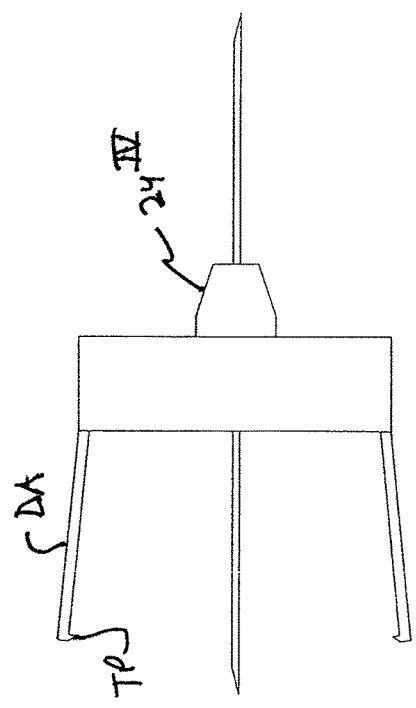
Figure 44:
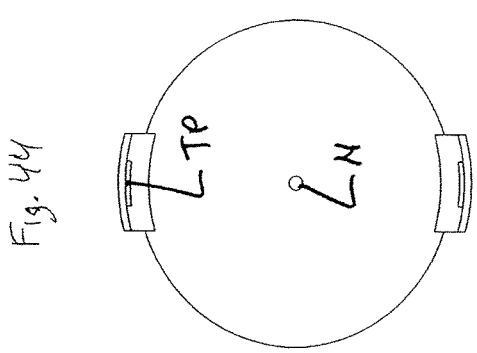

FIGS. 37-44 show another non-limiting embodiment of a pen needle, pen needle tip or pen needle assembly $100^{XI}$. The pen needle $100^{XI}$ includes the following main components similar to the previous embodiment: a body $10^{VI}$ which can be a one-piece body, a needle support $20^{IV}$ which can be a one-piece member, a double-ended hollow needle N and a system or arrangement of ensure more controlled axial movement of the support $20^{Iv}$. The system utilizes deflectable arms DA arranged on the support $20^{IV}$ which have tapered engaging projections TP that can engage with the external thread of the section 2. The advantage of this embodiment is that there is provided a more mechanical connection between the section 2 and the support $20^{IV}$. When the pen needle $100^{XI}$ is installed in the way shown in FIGS. 37 and 38, the arms DA are caused to deflect radially inwardly and the projections TP of the support $20^{IV}$ engaged with the thread of the section 2. This engagement increases the more the user slides on the pen needle. During removal of the pen needle $100^{XI}$ as shown in FIG. 39, the support $20^{IV}$ is drawn back until the projections TP automatically release from engagement with the thread of the section 2 as shown in FIG. 39. This can provide a more full proof way to ensure that the needle N is properly and fully retracted into the body $10^{XI}$ during removal from the device 1 and after use for injection. Although two arms DA are shown in FIGS. 42-44 and are arranged opposite one another (spaced 180 degrees apart from one another), the number of arms can be, for example, 3, 4, 5 or more. Moreover, each arm DA is normally deflected radially outwardly and can slide in a tapered recess TR (see FIGS. 40 and 41) and whose number can correspond to the number of arms DA.

Figure 45:
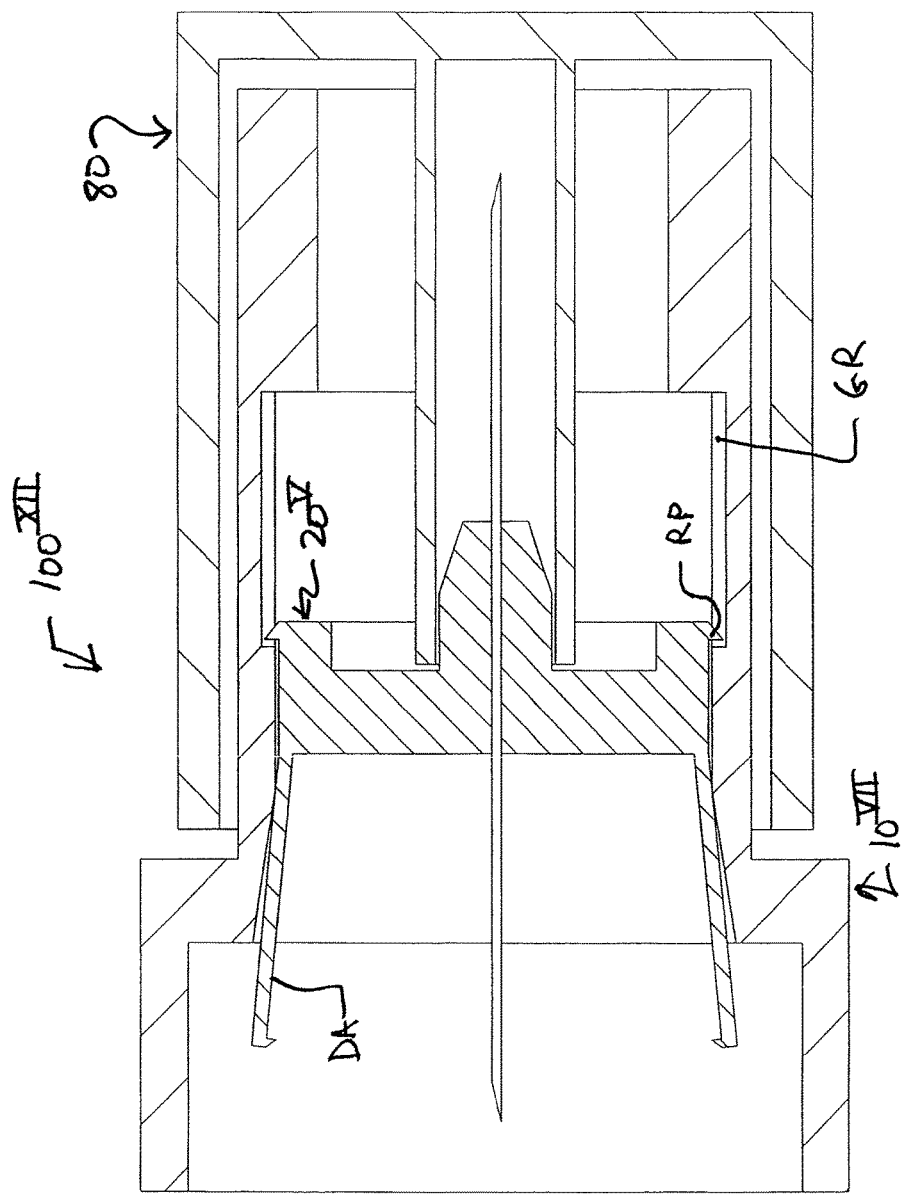
FIG. 45 shows another non-limiting embodiment and in an uninstalled and initial position.

FIG. 45 show an embodiment $100^{XII}$ wherein, in addition to using plural delectable arms DA, the support $20^V$ has movement limiting projections RP that slide within guide recesses GR. An outer cover 80 can advantageously be used to install the pen needle. An advantage of this embodiment is that during the installation, the skin puncturing end of the needle N projects beyond the skin engaging end of the pen needle body. However, the cover 80 ensures that the puncturing end is not exposed until the cover 80 is removed. During installation, the cover 80 is caused to more forward relative to the pen needle body, but remains installed thereon nonetheless.

Figure 46:
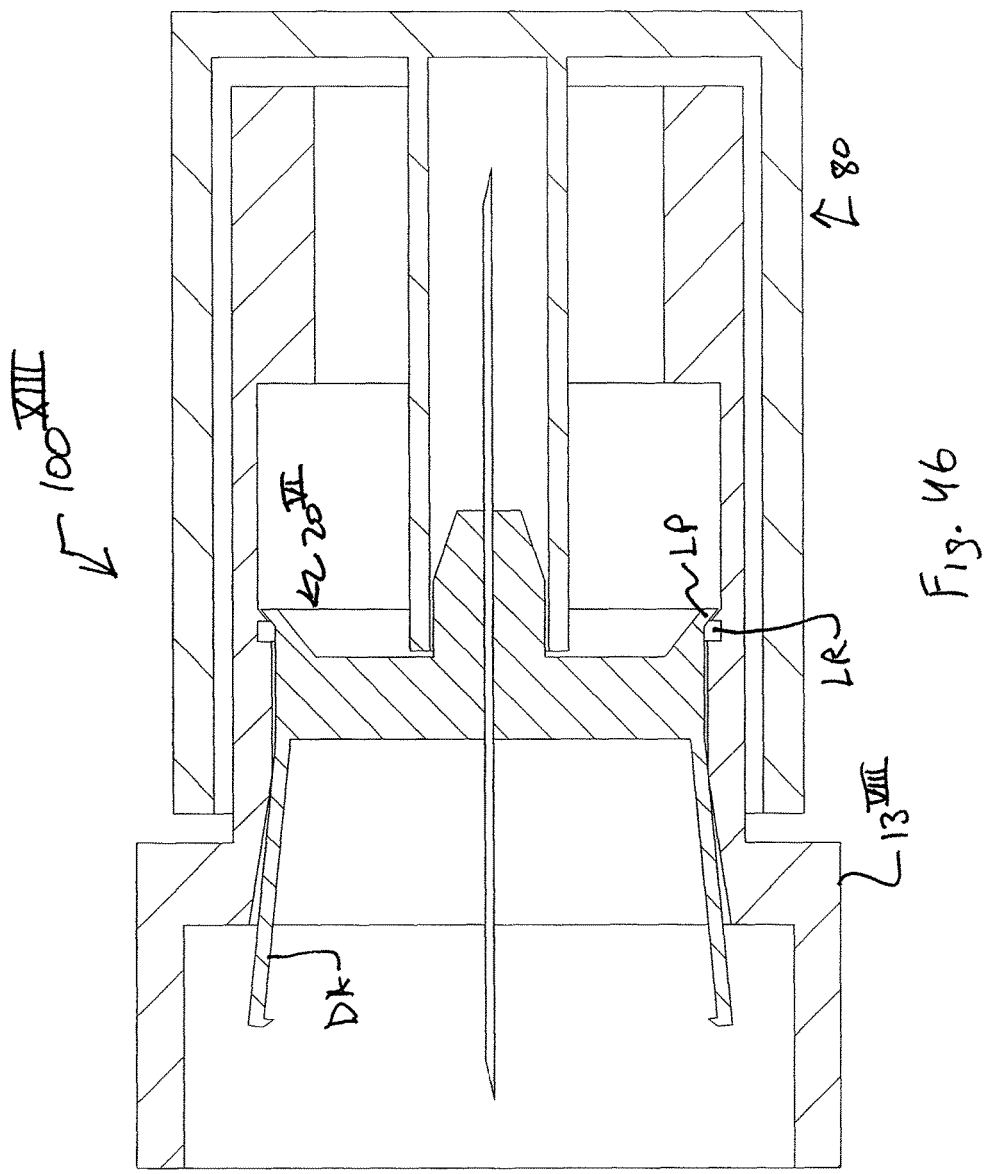
FIG. 46 shows another non-limiting embodiment and in an uninstalled and initial position.
Figure 47:
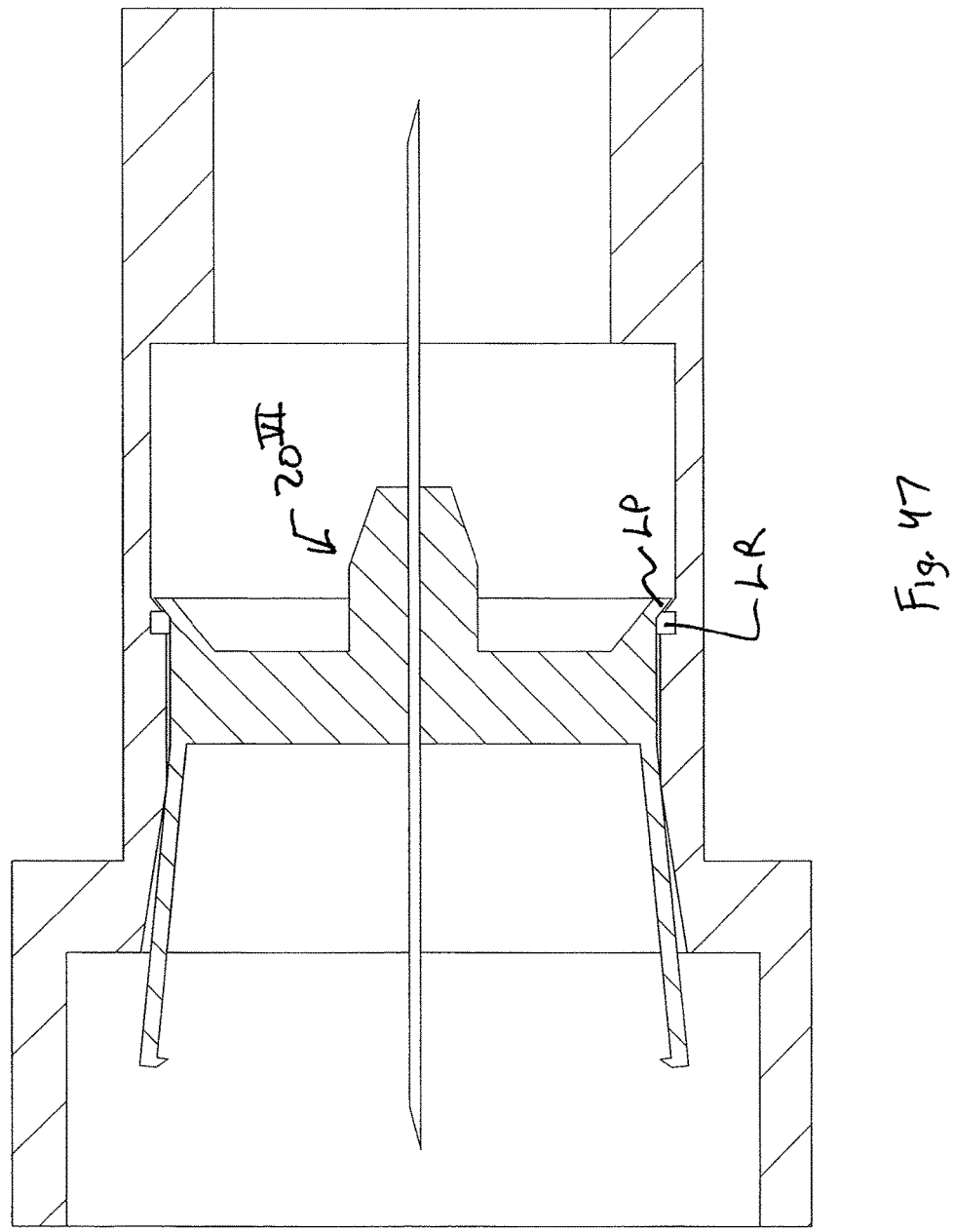
FIG. 47 shows the embodiment of FIG. 46 with an outer cover removed and in an installed state—the injection device is not shown for clarity purposes.
Figure 48:
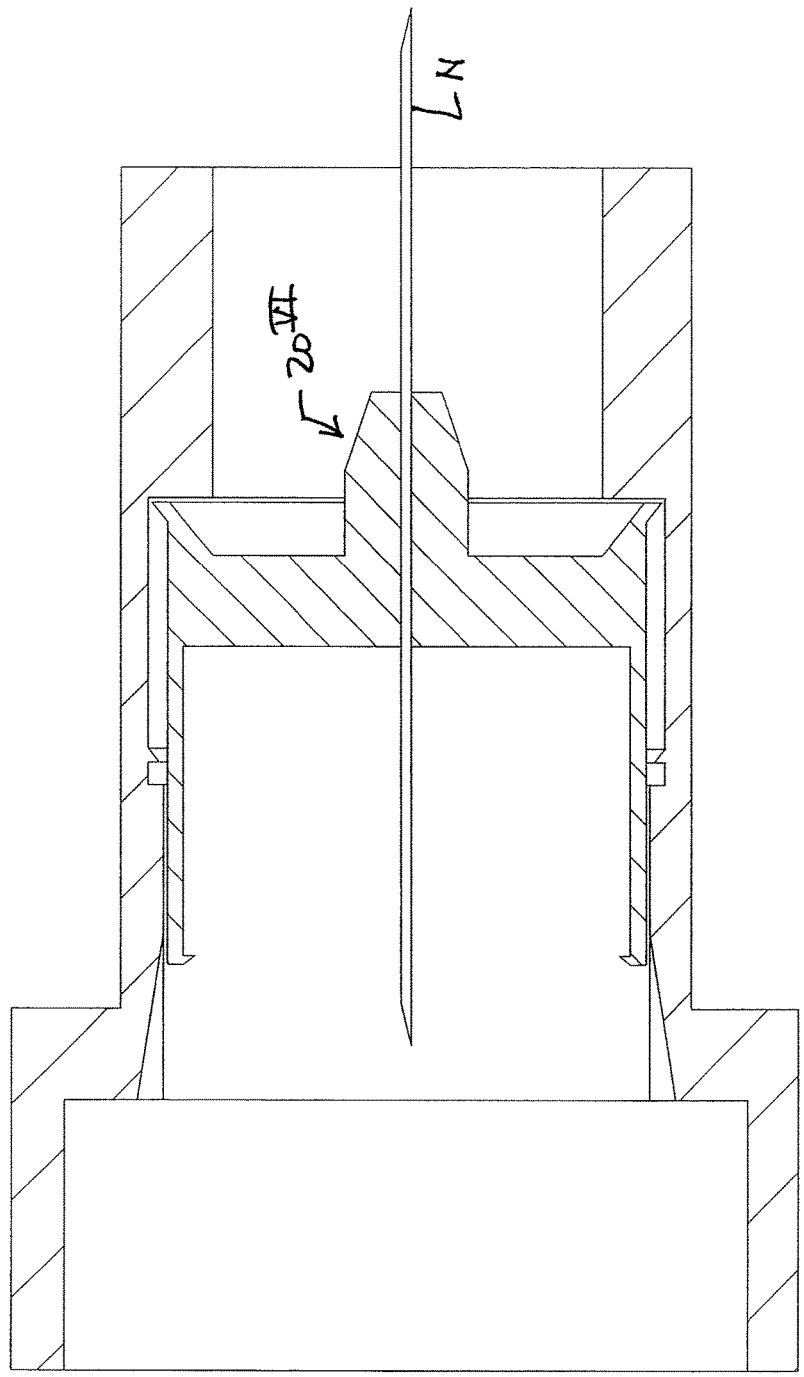
FIG. 48 shows the embodiment of FIG. 46 while in the injection or ready-to-injection position—the injection device is not shown for clarity purposes.
Figure 49:
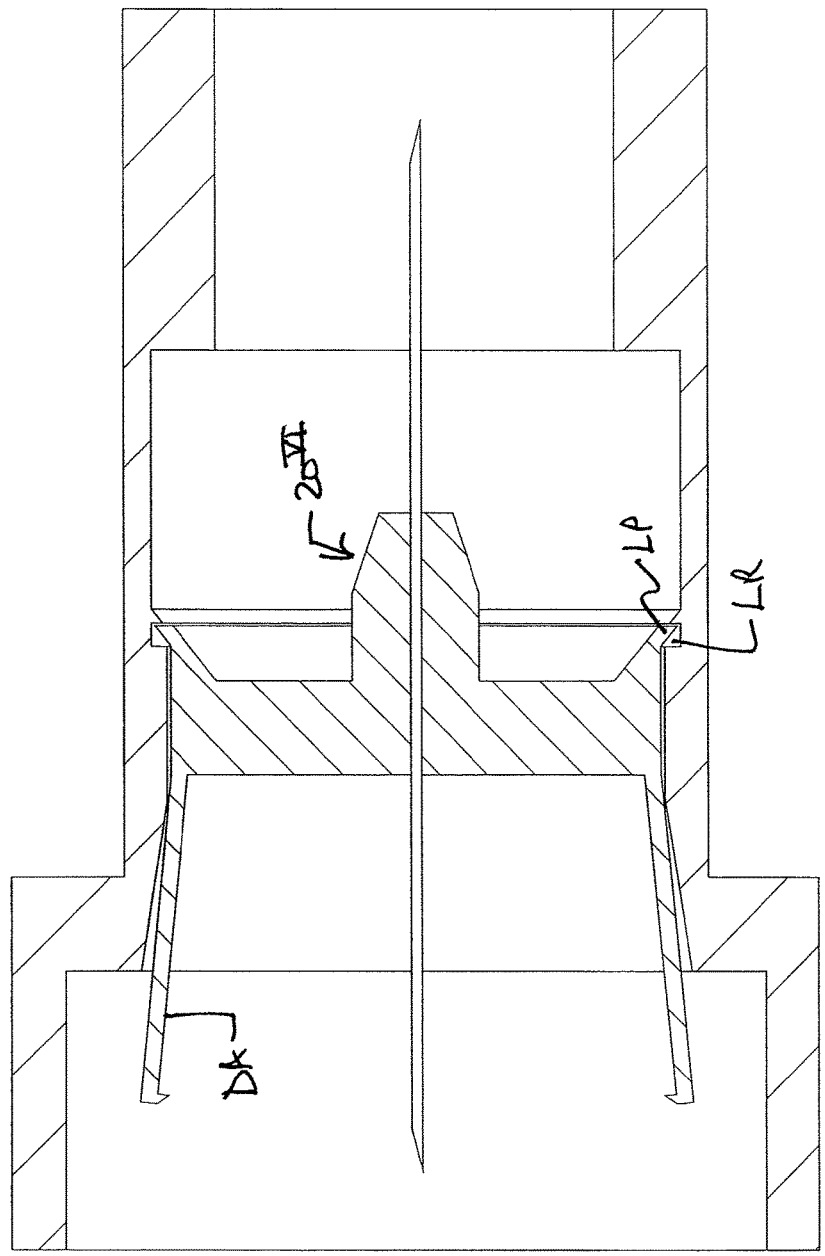
FIG. 49 shows the embodiment of FIG. 46 while in the post-use removed position.
Figure 50:
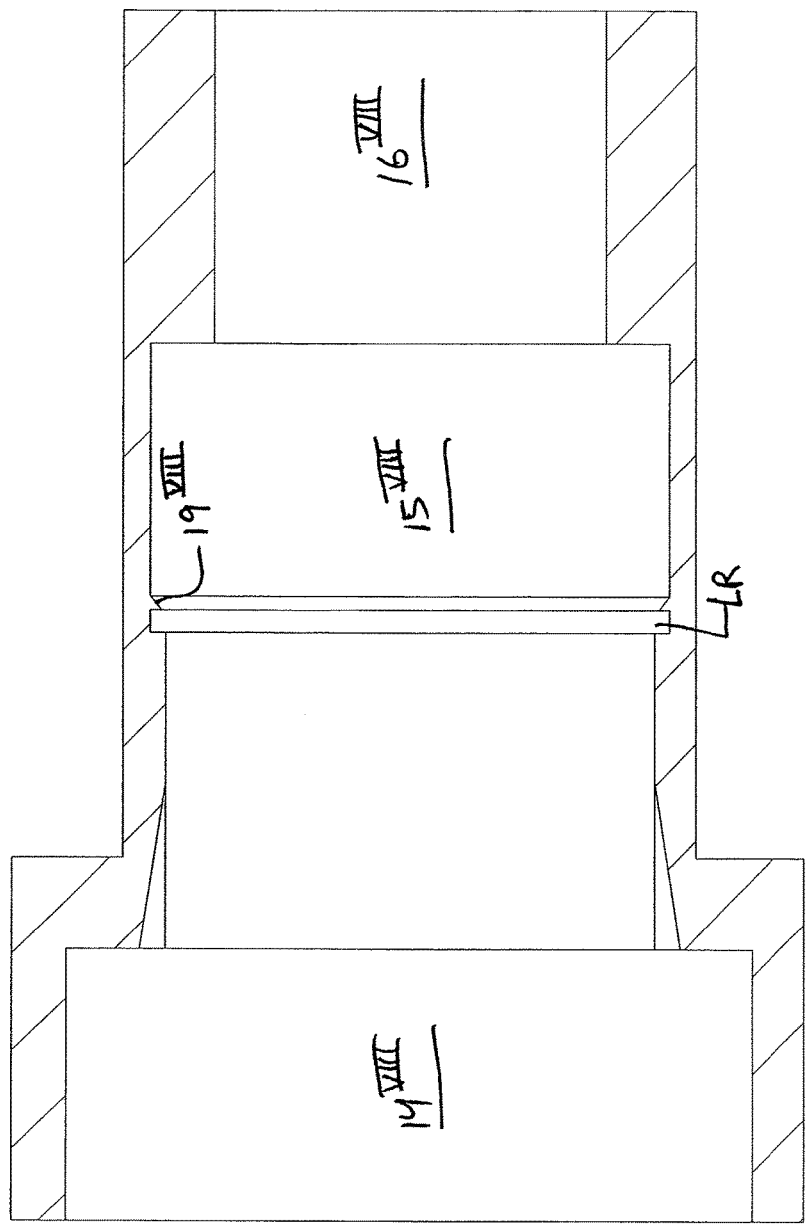
FIG. 50 shows a cross-section of the body used in the embodiment of FIG. 46.

FIGS. 46-50 show an embodiment $100^{XIII}$ using a continuous or annular locking projection LP on the support $20^{VI}$ which can lockingly engage with a locking recess LR. FIG. 46 shows the pen needle in a prior-use position. To install the same, a user can remove the cover 80 as shown in FIG. 47. During installation, the support $20^{VI}$ moves to the puncturing position shown in FIG. 48. During removal, the support $20^{VI}$ is moved to the locked position shown in FIG. 49. Alternatively, the outer cover 80 can advantageously be used to install the pen needle. An advantage of this embodiment is that during the installation, the skin puncturing end of the needle N projects beyond the skin engaging end of the pen needle body. However, the cover 80 ensures that the puncturing end is not exposed until the cover 80 is removed. During installation, the cover 80 is caused to more forward relative to the pen needle body, but remains installed thereon nonetheless.

FIG. 51 shows a variation of a previous non-limiting embodiment in that pen needle assembly $100^{XIV}$ can incorporate a user-adjustable penetration depth adjustment system or arrangement. The arrangement for depth adjustment utilizes a front member 90 which has an external thread that engages with an internal thread of the body $10^{IX}$. This allows the position of a skin engaging surface to change relative to a skin puncturing end of the needle N. When the user desires a deeper puncturing depth, the user merely rotates the member 90 relative to the body $10^{IX}$ in one direction to cause more of the member 90 to extend into the body $10^{IX}$. When the user desires a shallower puncturing depth, the user merely rotates the member 90 relative to the body $10^{IX}$ in an opposite direction to cause less of the member 90 to extend into the body $10^{IX}$. Indicia or indicators (not shown) may be utilized on the member 90 and body $10^{IX}$ to provide a visual indicator to the user as to the current depth setting position. Although not shown, a mechanism can also be utilized to releasably retain the member 90 in a desired depth setting position. The depth adjustment system shown in FIG. 51 can be used on any of the herein described embodiments.

The pen needle device or assembly shown and described above or herein can also utilize one or more features disclosed in the prior art documents expressly incorporated by reference herein. Furthermore, one or more of the various parts or components of the assembly can preferably be made as one-piece structures by e.g., injection molding, when doing so reduces costs of manufacture. Non-limiting materials for most of the parts include synthetic resins such as those approved for syringes or other medical devices. Furthermore, the invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A needle tip assembly for a pre-loaded syringe or a pen needle injection device, the needle tip assembly comprising:
a needle mounted to a needle support and comprising a first puncturing end projecting from a front side of the needle support and a second puncturing end projecting from a rear side of the needle support, where arranged on the needle support are deflectable arms having tapered engaging projections that can engage with an external thread on the pre-loaded syringe or the pen needle injection device;
a body sized and configured to receive therein the needle support and the needle;
the body comprising:
a front portion comprising a shoulder extending radially inward from an inner surface of the body;
a rear portion; and
an overall axial length that is greater than an axial length of the needle,
wherein, prior to the needle tip assembly being in an installed condition on the pre-loaded syringe or the pen needle injection device, each of:
the needle support is at a first position in the body with the deflectable arms deflecting radially outward beyond an outer surface of the needle support;
the front portion covers the first puncturing end; and
the rear portion covers the second puncturing end,
wherein, with the needle support in the first position in the body, the first puncturing end remains covered by the front portion, and during installation of the pre-loaded syringe or the pen needle injection device onto the second puncturing end, the inner surface of the body surrounding the outer surface of the needle support deflects the deflectable arms radially inward to engage the tapered engaging projections of the deflectable arms with the external thread as the body is axially moved relative to the needle support from the first position towards a second position where the front side of the needle support is in contact with the shoulder;
wherein, prior to removal from the pre-loaded syringe or the pen needle injection device, the body is at least axially movable relative to the needle support between the first position where the front portion covers the first puncturing end and the second position where the front portion does not cover the first puncturing end; and
wherein, during removal of the pre-loaded syringe or the pen needle infection device from the second puncturing end, the deflectable arms deflect radially outward to disengage the tapered engaging projections from the external thread as the body is axially moved relative to the needle support towards the first position.

2. The needle tip assembly of claim 1, wherein the needle tip assembly is a single-use needle tip assembly.

3. The needle tip assembly of claim 1, wherein the body is a one-piece body comprising tapered recesses that align with the deflectable arms.

4. The needle tip assembly of claim 1, wherein the needle support is a one-piece body comprising locking projections that can lock or snap into a locking recess arranged in the inner surface of the body thereby limiting movement of the needle support after removal of the pre-loaded syringe or the pen needle injection device.

5. The needle tip assembly of claim 1, wherein the needle support is generally disk-shaped comprising a central portion that is substantially perpendicular to the needle and extends radially outward from the needle to an inner wall of the body.

6. The needle tip assembly of claim 1, wherein the needle support is a synthetic resin member.

7. The needle tip assembly of claim 1, wherein the needle is a double-ended hollow metal needle having similarly shaped opposite puncturing ends.

8. The needle tip assembly of claim 1, further comprising a one-piece packaging cover sized and configured to contain therein the body having the needle support and the needle installed in a prior-use configuration, the one-piece packaging cover comprising a closed end that is tapered to cover the front portion of the body and an open end that is sealable by a removable seal.

9. The needle tip assembly of claim 1, further comprising a one-piece tubular packaging cover comprising a closed end and an open end, and a removable seal comprising a pull-tab arrangement, wherein the one-piece tubular packaging cover is adapted to encircle and store therein the body, the needle support and the needle in a sterile condition when the open end is sealed by the removable seal.

10. A needle tip assembly for a pre-loaded syringe or a pen needle injection device, the needle tip assembly comprising:
a needle mounted to a needle support and comprising a first puncturing end projecting from a front side of the needle support and a second puncturing end projecting from a rear side of the needle support, where arranged on the needle support are deflectable arms having tapered engaging projections that can engage with an external thread on the pre-loaded syringe or the pen needle injection device;
a body sized and configured to receive therein the needle support and comprising:
a front portion;
a rear portion; and
an overall axial length that is greater than an axial length of the needle,
wherein, prior to the needle tip assembly being installed on the pre-loaded syringe or the pen needle injection device, each of:
the needle support is at a first position in the body with the deflectable arms deflecting radially outward beyond an outer surface of the needle support;
the front portion covers the first puncturing end; and
the rear portion covers the second puncturing end,
wherein the needle support remains in the first position in the body, and the first puncturing end remains covered by the front portion, during full installation of the pre-loaded syringe or the pen needle injection device onto the second puncturing end, where the pre-loaded syringe or the pen needle injection device is fully installed when the second puncturing end projecting from a rear surface of the rear side of the needle support is fully inserted into the pre-loaded syringe or the pen needle injection device and the pre-loaded syringe or the pen needle injection device is in contact with the rear surface, and an inner surface of the body surrounding the outer surface of the needle support deflects the deflectable arms radially inward to engage the tapered engaging projections of the deflectable arms with the external thread as the body is axially moved relative to the needle support from the first position towards a second position; and wherein, after injection and while installed on the pre-loaded syringe or the pen needle injection device, the body is at least axially movable relative to the needle support between the second position where the front portion does not cover the first puncturing end and the first position wherein the front portion covers the first puncturing end, and the deflectable arms deflect radially outward to disengage the tapered engaging projections from the external thread as the body is axially moved relative to the needle support towards the first position.

11. The needle tip assembly of claim 10, wherein the needle tip assembly is a single-use needle tip assembly comprising locking projections that can lock or snap into a locking recess arranged in the inner surface of the body thereby limiting movement of the needle support after removal of the pre-loaded syringe or the pen needle injection device.

12. The needle tip assembly of claim 10, wherein the body is a one-piece body having a generally circular cross-section comprising tapered recesses that align with the deflectable arms.

13. The needle tip assembly of claim 10, wherein the needle support is at least one of:
  a one-piece body non-removably coupled to a central area of the needle; and
  generally disk-shaped and has a circular cross-section.

14. The needle tip assembly of claim 10, wherein the rear portion of the body always covers the second puncturing end and the front portion of the body is movable between an initial position corresponding to the first position where the first puncturing end is covered, a retracted position corresponding to the second position where the first puncturing end is exposed, and a post-use position where the needle support is secured in substantially the first position thereby covering the first puncturing end.

15. The needle tip assembly of claim 14, wherein the needle support comprises at least one locking element configured to lock the body in the post-use position.

16. The needle tip assembly of claim 10, further comprising a packaging cover sized and configured to contain therein the body, the needle support and the needle in a prior-use configuration.

17. The needle tip assembly of claim 10, further comprising a packaging cover and removable pull-tab arrangement adapted to store therein the body, the needle support and the needle in a sterile condition.

18. The needle tip assembly of claim 10, wherein the needle support and the body are capable of being in locking engagement with one another so as to prevent re-use of the needle tip assembly.

19. The needle tip assembly of claim 10, wherein the needle support comprises at least one retaining projection that engages with the body to limit axial movement of the body relative to the needle support when the needle tip assembly is in an installed condition.

20. A single-use needle tip assembly for a pre-loaded syringe or a pen needle injection device, the needle tip assembly comprising:
  a needle mounted to a needle support and comprising a first puncturing end projecting from a front side of the needle support and a second puncturing end projecting from a rear side of the needle support, where arranged on the needle support are deflectable arms having tapered engaging projections that can engage with an external thread on the pre-loaded syringe or the pen needle injection device;
  a body sized and configured to receive therein the needle support and comprising:
    a front portion;
    a rear portion; and
    an overall axial length that is greater than an axial length of the needle,
  wherein, prior to the needle tip assembly being installed on the pre-loaded syringe or the pen needle injection device, each of:
    the needle support is at a first position in the body with the deflectable arms deflecting radially outward beyond an outer surface of the needle support;
    the front portion covers the first puncturing end; and
    the rear portion covers the second puncturing end,
  wherein the needle support remains in the first position in the body, and the first puncturing end remains covered by the front portion, during installation of the pre-loaded syringe or the pen needle injection device onto the second puncturing end with the external thread located between the deflectable arms; and
  wherein, prior to the needle tip assembly being removed from the pre-loaded syringe or the pen needle injection device, each of:
    the body moves relative to the needle support in one direction to a retracted position where the front portion does not cover the first puncturing end, where an inner surface of the body surrounding the outer surface of the needle support deflects the deflectable arms radially inward to engage the tapered engaging projections of the deflectable arms with the external thread during movement to the retracted position;
    the body moves relative to the needle support in another direction to a post-use position where the front portion covers the first puncturing end, where the deflectable arms deflect radially outward to disengage the tapered engaging projections from the external thread during movement to the post-use position; and
    the rear portion covers the second puncturing end in both the retraced and post-use positions.

\* \* \* \* \*